US010842402B2

(12) United States Patent
Adachi et al.

(10) Patent No.: US 10,842,402 B2
(45) Date of Patent: Nov. 24, 2020

(54) DETERMINATION SYSTEM, CONTROL SIGNAL OUTPUT SYSTEM, REHABILITATION SYSTEM, DETERMINATION METHOD, CONTROL SIGNAL OUTPUT METHOD, AND RECORDING MEDIUM

(71) Applicant: Panasonic Intellectual Property Management Co., Ltd., Osaka (JP)

(72) Inventors: Shinobu Adachi, Nara (JP); Jun Ozawa, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1384 days.

(21) Appl. No.: 14/965,597

(22) Filed: Dec. 10, 2015

(65) Prior Publication Data
US 2016/0198971 A1 Jul. 14, 2016

(30) Foreign Application Priority Data

Jan. 9, 2015 (JP) .................. 2015-003090

(51) Int. Cl.
*A61B 5/0478* (2006.01)
*A61B 5/048* (2006.01)
(Continued)

(52) U.S. Cl.
CPC ............ *A61B 5/0478* (2013.01); *A61B 5/048* (2013.01); *A61B 5/6817* (2013.01);
(Continued)

(58) Field of Classification Search
CPC ....... A61B 5/04; A61B 5/0476; A61B 5/0478; A61B 5/6814; A61B 5/6817;
(Continued)

(56) References Cited

U.S. PATENT DOCUMENTS

2003/0195588 A1* 10/2003 Fischell .................. A61N 2/02
607/55
2005/0131311 A1* 6/2005 Leuthardt ................ A61F 4/00
600/545
2012/0029336 A1* 2/2012 Terada ............... A61B 5/04004
600/383

(Continued)

FOREIGN PATENT DOCUMENTS

JP  2010-051356     3/2010
JP  2012-217721    11/2012
JP  2012217721 A  * 11/2012

OTHER PUBLICATIONS

Looney, David, "The In-the-Ear Recording Concept", Dec. 11, 2012, IEEE Pulse, Nov./Dec. 2012 (Year: 2012).*

(Continued)

*Primary Examiner* — Samchuan C Yao
*Assistant Examiner* — Matthew Standard
(74) *Attorney, Agent, or Firm* — Wenderoth, Lind & Ponack, L.L.P.

(57) ABSTRACT

A determination system includes a head electrode that is located on a left head portion of a user when an intention of the user to move a portion on a right side of a body of the user is detected and that is located on a right head portion of the user when an intention of the user to move a portion on a left side of the body of the user is detected; an ear hole electrode that is located in an ear hole of the user; an electroencephalogram signal measurer that obtains a voltage between the head electrode and the ear hole electrode; and a determiner that determines whether or not a change in the voltage includes the intention to move the portion on the right side of the body or the intention to move the portion on the left side of the body.

21 Claims, 16 Drawing Sheets

(51) Int. Cl.
    *G06F 19/00*     (2018.01)
    *A61B 5/00*     (2006.01)
    *A61H 1/02*     (2006.01)

(52) U.S. Cl.
    CPC ......... *A61H 1/0266* (2013.01); *A61H 1/0285* (2013.01); *G06F 19/325* (2013.01); *A61B 5/7275* (2013.01); *A61B 2505/09* (2013.01); *A61H 2201/1207* (2013.01); *A61H 2201/164* (2013.01); *A61H 2201/165* (2013.01); *A61H 2201/1635* (2013.01); *A61H 2201/5007* (2013.01); *A61H 2230/045* (2013.01); *A61H 2230/105* (2013.01)

(58) Field of Classification Search
    CPC .......... A61B 2205/09; A61H 2201/165; A61H 2201/5007; A61H 2201/5058; A61H 2230/10; A61H 2230/105; A61H 1/02; A61H 1/0266–0288
    See application file for complete search history.

(56) References Cited

U.S. PATENT DOCUMENTS

2012/0059273 A1*   3/2012   Meggiolaro ........... A61B 5/048
                                                     600/544
2012/0172744 A1    7/2012   Kato et al.
2015/0091791 A1*   4/2015   Segal .................... G06F 16/436
                                                     345/156

OTHER PUBLICATIONS

Teplan, M., "Fundamentals of EEG Measurement", Measurement Science Review, vol. 2, Section 2, 2002. (Year: 2002).*

Agur, M.R. Anne and Dalley, F. Arthur "Grant's Atlas of Anatomy", Published 2013 by Lippincott Williams & Wilkins, Thirteenth edition, p. 711 (Year: 213).*

Crone, Nathan E., et. al, "Functional mapping of human sensorimotor cortex with electrocorticographic specral analysis", Brain 1998, 121, 2271-2299 (Year: 1991).*

* cited by examiner

FIG. 4

| ELECTRODE NUMBER | RIGHT-HAND CONDITION | LEFT-HAND CONDITION |
|---|---|---|
| 1 | C3 | C4 |
| 2 | C3L | C4L |
| 3 | LEFT AURICULAR CONCHA | RIGHT AURICULAR CONCHA |
| 4 | UPPER PORTION OF LEFT EAR HOLE | UPPER PORTION OF RIGHT EAR HOLE |
| 5 | FRONT PORTION OF LEFT EAR HOLE | FRONT PORTION OF RIGHT EAR HOLE |
| 6 | RIGHT AURICULAR CONCHA | LEFT AURICULAR CONCHA |
| 7 | UPPER PORTION OF RIGHT EAR HOLE | UPPER PORTION OF LEFT EAR HOLE |
| 8 | FRONT PORTION OF RIGHT EAR HOLE | FRONT PORTION OF LEFT EAR HOLE |
| REFERENCE | LEFT MASTOID | RIGHT MASTOID |
| EARTH | RIGHT MASTOID | LEFT MASTOID |

DETERMINATION SYSTEM, CONTROL SIGNAL OUTPUT SYSTEM, REHABILITATION SYSTEM, DETERMINATION METHOD, CONTROL SIGNAL OUTPUT METHOD, AND RECORDING MEDIUM

BACKGROUND

1. Technical Field

The present disclosure relates to a technique for measuring event-related desynchronization (ERD) in brain waves that is induced by a motor intention.

2. Description of the Related Art

ERD is a phenomenon in which, in the case of intending to perform a movement or actually performing a movement, a voltage strength in the $\alpha$ band and/or a voltage strength in the $\beta$ band of brain waves at the vicinity of the motor area of the head decreases compared to that in a resting state. It is known that the frequency band in which ERD occurs varies among individuals, that is, ERD may occur only in the $\alpha$ band, only in the $\beta$ band, or in both of the $\alpha$ and $\beta$ bands.

Japanese Unexamined Patent Application Publication No. 2012-217721 discloses a rehabilitation apparatus that measures an electroencephalogram (EEG) signal at the vicinity of the motor area corresponding to a target portion of rehabilitation, detects ERD on the basis of a change over time in signal strength of a certain frequency component of the measured EEG signal, and thereby moves an attachment attached to a paralyzed portion. Specifically, the rehabilitation apparatus determines, at an interval of 50 ms, whether or not ERD exists and, if ERD is detected, immediately operates a motor to give feedback to a patient. Accordingly, the time lag between a motor intention and an actual movement can be reduced and thereby effective rehabilitation can be performed.

SUMMARY

However, in the method disclosed in Japanese Unexamined Patent Application Publication No. 2012-217721, ERD is not detected regardless of a user's motor intention in some cases. ERD detection is a first important step in brain machine interface (BMI) rehabilitation using an electroencephalogram (EEG), and thus it is considered that low ERD detection accuracy may result in a decrease in rehabilitation effect.

One non-limiting and exemplary embodiment provides a determination system for detecting ERD with high accuracy.

In one general aspect, the techniques disclosed here feature a determination system including a head electrode that is located on a left head portion of a user when an intention of the user to move a portion on a right side of a body of the user is detected and that is located on a right head portion of the user when an intention of the user to move a portion on a left side of the body of the user is detected; an ear hole electrode that is located in an ear hole of the user; an electroencephalogram signal measurer that obtains a voltage between the head electrode and the ear hole electrode; and a determiner that determines whether or not a change in the voltage includes the intention of the user to move the portion on the right side of the body of the user or the intention of the user to move the portion on the left side of the body of the user.

According to an embodiment of the present disclosure, ERD can be detected with high accuracy.

It should be noted that general or specific embodiments may be implemented as a system, a method, an integrated circuit, a computer program, a computer-readable recording medium, or any selective combination thereof. The computer-readable recording medium includes a nonvolatile recording medium, for example, a compact disc-read only memory (CD-ROM) or the like.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4 is a diagram illustrating electrode positions and electrode numbers for individual conditions;

DETAILED DESCRIPTION

Figure 1:
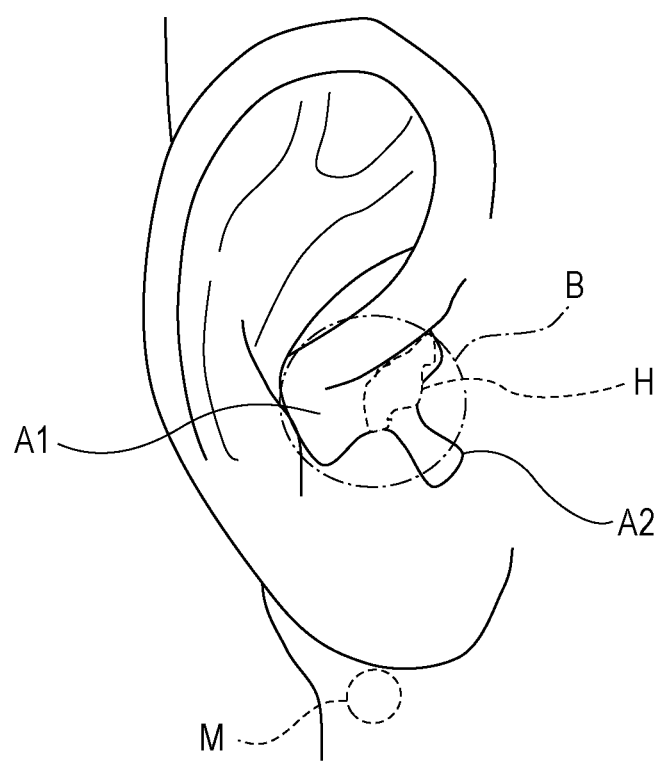
FIG. 1 is a diagram illustrating a shape of a right ear.

In this specification, an "ear hole" is a region including a tympanic membrane, an external auditory canal, and an auricular concha. An example of the ear hole is a region including a region H that includes an auricular concha and an external auditory canal, a cavum conchae A1, and an intertragic notch A2 (see FIG. 1). The ear hole may be a hollow portion included in a region B illustrated in FIG. 1. The right side of a body is a portion on the right side of a human body and includes, for example, a right head portion, a right ear, a right mastoid, a right ear hole, a right hand, a right arm, and a right foot. The left side of a body is a portion on the left side of a human body and includes, for example, a left head portion, a left ear, a left mastoid, a left ear hole, a left hand, a left arm, and a left foot.

Before describing an embodiment of the present disclosure, matters considered by the inventors will be described.

It is said that about 300 thousand people suffer cerebral stroke per year in Japan. Cerebral stroke may leave a patient with a paralyzed hand or foot. The patient undergoes rehabilitation to improve the paralysis.

Paralysis has at least the following two degrees (A) and (B). In accordance with the degrees of paralysis, different rehabilitation programs are proposed.

(A) When a patient tries to move a paralyzed portion, a myoelectric potential is generated by innervated muscles but the paralyzed portion does not move. In this case, the myoelectric potential of the patient is measured and motor nerves connected to the innervated muscles are electrically stimulated in accordance with the level of the measured myoelectric potential, and thereby the muscles are forcefully constricted.

(B) Even when a patient tries to move a paralyzed portion, no myoelectric potential is generated by innervated muscles. In this case, the foregoing rehabilitation method using a myoelectric potential is inappropriate. Thus, as described in Japanese Unexamined Patent Application Publication No. 2012-217721, a motor intention of the patient is extracted by using ERD in brain waves as an index, an attachment attached to the paralyzed portion is moved by a motor or the like, and thereby the paralyzed portion is moved. This method is called brain machine interface (BMI) rehabilitation using an electroencephalogram (EEG).

An EEG signal acquisition system according to an embodiment of the present disclosure detects ERD with high accuracy by using a change in the potential difference between one measurement electrode located on a head and one measurement electrode located in an ear hole. The present disclosure is based on an ERD detection characteristic that has been found out through experiments conducted by the inventors. Before describing an exemplary embodiment of the present disclosure, a detailed description will be given of the experiments conducted by the inventors, the results of the experiments, and knowledge obtained through the experiments. After that, a description will be given of an outline of an ERD measurement system according to an embodiment and the configuration and operation thereof.

Outline of Experiments

The inventors conducted ERD measurement experiments by locating electrodes in a motor area of a head and an ear hole in order to specify the electrode positions where ERD induced by a motor intention can be optimally detected. As a result, the inventors found that the ERD detection rate is higher in the case of using, as an index, a change in a potential difference in brain waves measured at one point near the motor area of the head and one point in the ear hole, than in the case of using a change in a potential difference in brain waves measured at two points near the motor area of the head. The higher accuracy of ERD detection may result in higher efficiency of rehabilitation in which a motor intention of a user is extracted by using ERD as an index, such as a BMI rehabilitation system using an EEG.

Experiment Method

The test subject was an adult male (36 years old) with no history of cerebral stroke.

The test subject was requested to alternately repeat five-second relaxation (referred to as a relax section) and five-second finger extension imaging (referred to as an imaging section) in accordance with a sound stimulation indicating the timing at which tasks are to be changed. An instruction was provided to the test subject to loosen up the whole body as much as possible and relax in the relax section and to image extending fingers slowly for five seconds while keeping the hands squeezed lightly in the imaging section. A right-hand condition of performing finger extension imaging of the right hand and a left-hand condition of performing finger extension imaging of the left hand were provided. Twenty repetitions were regarded as one set, and three sets of experiments were performed for each condition. That is, in a case where a relax section and an imaging section following the relax section are regarded as one process (one trial), one set includes twenty processes (twenty trials). Three sets of experiments under the right-hand condition and three sets of experiments under the left-hand condition were performed.

Figure 2A:
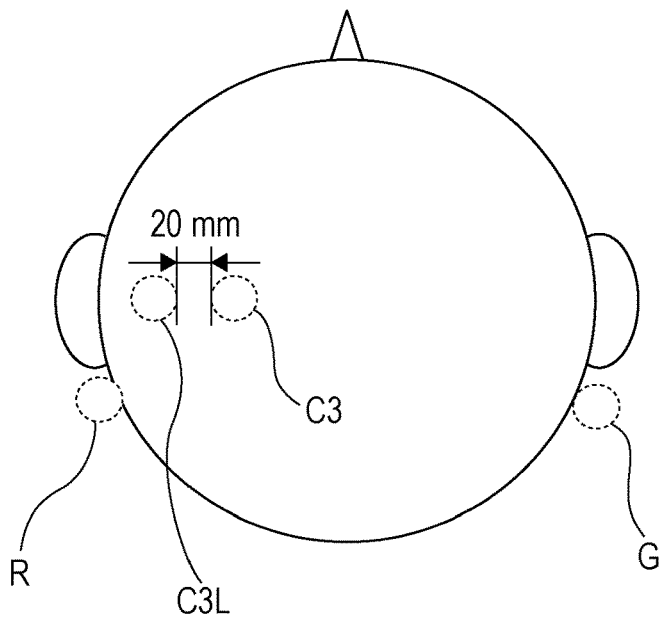
FIG. 2A is a schematic diagram illustrating locations of head electrodes under a right-hand condition.
Figure 2B:
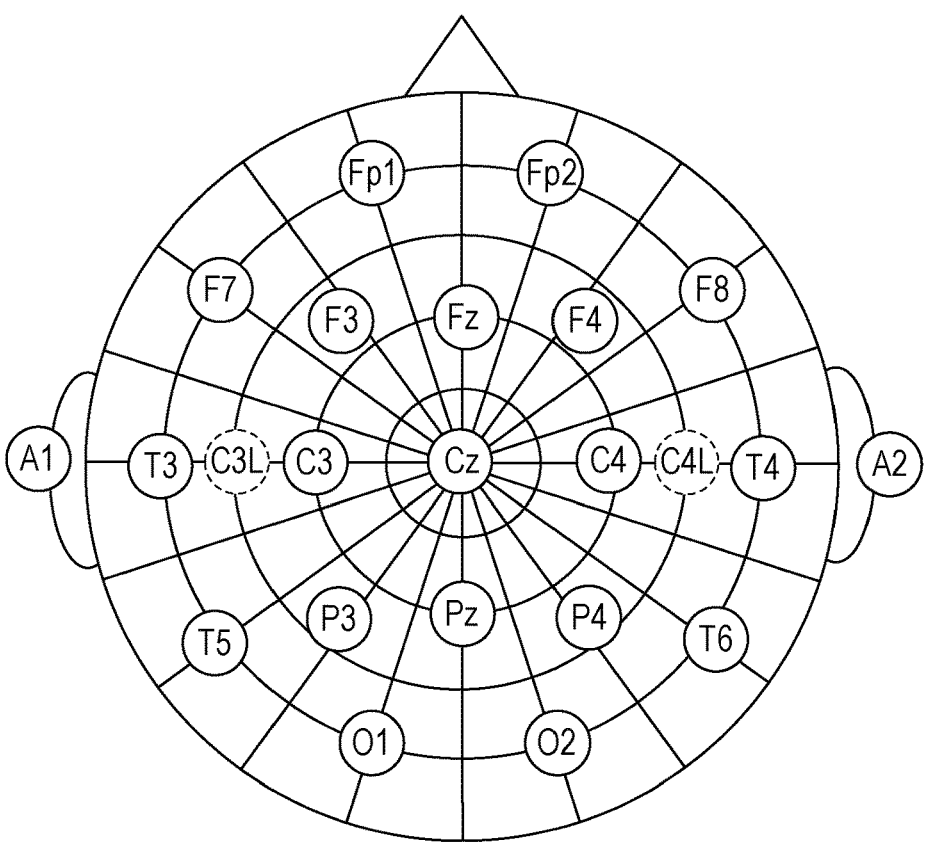
FIG. 2B is a diagram illustrating electrode locations according to the international 10-20 system.

In the experiments, electrodes were located at two points on the head near the motor area corresponding to the hand as a target of movement imaging (hereinafter may be referred to as a "movement imaging hand") and six points in the ear holes (three points in each of the right and left ear holes), and brain waves were recorded. FIG. 2A schematically illustrates the locations of head electrodes under the right-hand condition. In the case of the right-hand condition, head electrodes were attached to a position C3 specified by the international 10-20 system and a position 20 mm to the left of the position C3 (referred to as a position C3L). FIG. 2B illustrates the electrode locations specified by the international 10-20 system. The position C3L is also illustrated for reference. A reference electrode R was attached to a left mastoid (represented by R in FIG. 2A) on the same side as the head electrodes, whereas an earth (ground) G was attached to a right mastoid (represented by G in FIG. 2A) on the side opposite to the head electrodes.

On the other hand, in the case of the left-hand condition, head electrodes were attached to a position C4 specified by the international 10-20 system and a position 20 mm to the right of the position C4 (referred to as a position C4L). FIG. 2B also illustrates the position C4L for reference. A reference electrode was attached to the right mastoid on the same side as the head electrodes, whereas an earth was attached to the left mastoid on the side opposite to the head electrodes.

A mastoid is a portion below an ear (a portion below the base of the ear). FIG. 1 illustrates a position M of the mastoid.

Figure 3A:
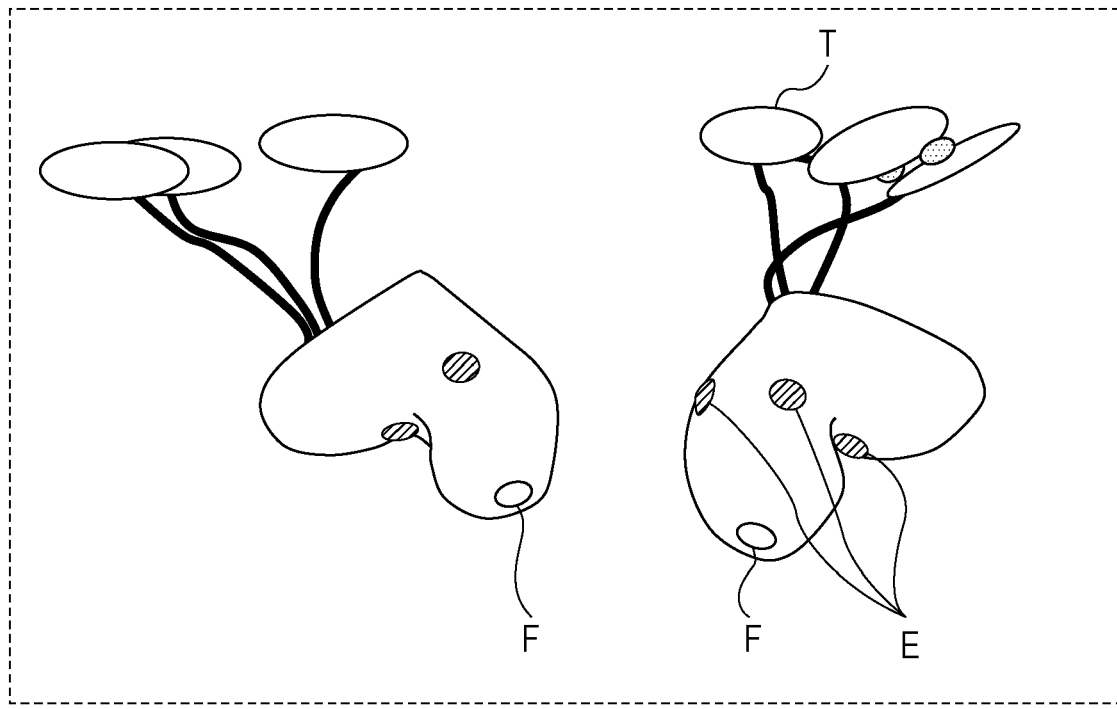
FIG. 3A is a diagram illustrating ear molds for right and left ears made to measure brain waves in ear holes.
Figure 3B:
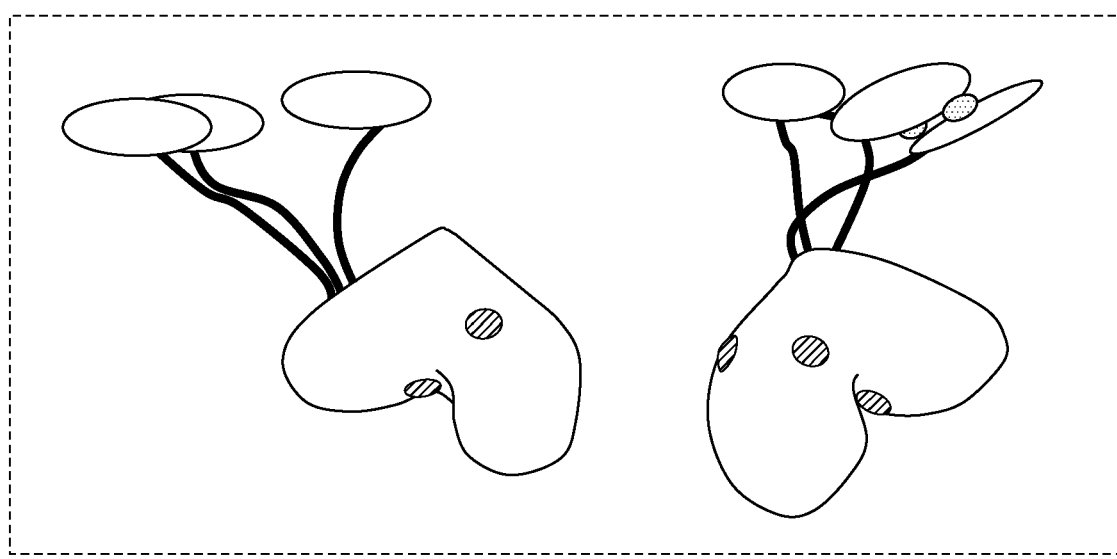
FIG. 3B is a diagram illustrating ear molds for right and left ears made to measure brain waves in ear holes.

FIGS. 3A and 3B each illustrate ear molds for the right and left ears made to measure brain waves in the ear holes. The ear molds were made on the basis of casts of the ears of the test subject taken in advance. As illustrated in FIG. 3A, each of the right and left ear molds has ear hole electrodes E located at three positions. The ear hole electrodes E are made of a silver-silver chloride material having a diameter of 3 mm. Each ear mold has an ear hole electrode at a position that comes into contact with the auricular concha, an ear hole electrode at a position that comes into contact with the front side (face side) above a first curve of the external auditory canal, and an ear hole electrode at a position that comes into contact with the upper side (head top side) thereof. The positions of the ear hole electrodes are not limited thereto, but at least need to be the positions at which the ear mold comes into contact with the ear hole.

The difference between the ear molds illustrated in FIG. 3A and the ear molds illustrated in FIG. 3B is the presence/absence of holes F. Other than this point, both of the ear molds are the same. A terminal T illustrated in FIG. 3A is connected to an operation amplifier circuit (not illustrated) for measuring a potential.

To make the ear molds illustrated in FIG. 3A, a hole was intentionally provided at a cross-sectional portion of the external auditory canal for two reasons. One reason is to ensure the permeability of the ear hole and suppress an influence of sweat on measurement of brain waves. In the case of measuring brain waves by locating a plurality of electrodes in ear molds with a small surface area, the distances between electrodes are short. This may cause a short circuit of the electrodes via sweat. In this case, brain waves are not correctly recorded. The other reason is to pass external sound information. At a site of BMI rehabilitation using an EEG, a physical therapist communicates with a user, for example, informs the user of the progress or gives the user encouraging words. Also, notification about the start timings of a relax section and an imaging section can be given by using sound information. An example of the diameter of the through hole F is about 3 mm or more and 5 mm or less. The diameter of the through hole F may be larger or smaller.

In an environment in which the necessity of the above-described through hole F is low, the ear molds without holes illustrated in FIG. 3B may be made and used. FIG. 4 illustrates electrode positions and electrode numbers for each condition. The head electrodes correspond to electrode numbers 1 and 2, and the three ear hole electrodes of each of the right and left ears correspond to electrode numbers 3 to 8.

As illustrated in FIG. 4, the positions of the measurement electrodes for the head and ear holes and the positions of the reference electrode and earth electrode for the left-hand condition are opposite to those for the right-hand condition. Accordingly, data for the right-hand condition and the left-hand condition can be analyzed for each electrode number.

As an electroencephalograph, Polymate AP1124 (made by TEAC) was used. A sampling frequency of 1000 Hz and a time constant of 1 second were used. A band-path filter of 1 to 30 Hz in offline was applied.

The presence/absence of ERD was determined on the basis of a brain waveform (change in voltage) obtained through measurement. In consideration of the time lag at the switching between a relax section and an imaging section, data for the first one second and the last one second in five seconds was removed, and frequency analysis was performed on data for the residual three seconds. Then, an average value of intensity in the $\alpha$ waveband of brain waves in the relax section, an average value of intensity in the $\beta$ waveband of brain waves in the relax section, an average value of intensity in the $\alpha$ waveband of brain waves in the imaging section, and an average value of intensity in the $\beta$ waveband of brain waves in the imaging section were calculated. The $\alpha$ waveband ranged from 8 to 12 Hz, whereas the $\beta$ waveband ranged from 13 to 26 Hz. Further, by using Pr$\alpha$ representing the average value of intensity in the $\alpha$ waveband of brain waves in the relax section and Pi$\alpha$ representing the average value of intensity in the $\alpha$ waveband of brain waves in the imaging section just after the relax section, an ERD change rate in the $\alpha$ waveband (Pr$\alpha$−i$\alpha$)/Pr$\alpha$×100 was calculated. Also, by using Pr$\beta$ representing the average value of intensity in the $\beta$ waveband of brain waves in the relax section and Pi$\beta$ representing the average value of intensity in the $\beta$ waveband of brain waves in the imaging section just after the relax section, an ERD change rate in the $\beta$ waveband (Pr$\beta$−Pi$\beta$)/Pr$\beta$×100 was calculated.

To determine the optimum electrode pair (a combination of measurement positions) for ERD detection, (1) the ERD change rates of electric signals (potential difference signals) between the individual measurement electrodes and the reference electrode were calculated and (2) the ERD change rates of electric signals (potential difference signals) between the measurement electrodes in individual 28 combinations, each combination including two different measurement electrodes, were calculated. In a case where the ERD change rate is a positive value or zero, it was determined that ERD occurred in the imaging section. The determination result about the presence/absence of ERD was compared with a determination result obtained by using an electric signal (potential difference signal) between two electrodes on the head at typical electrode positions in a method according to the related art. Note that a potential difference may be referred to as a voltage.

Figure 5:
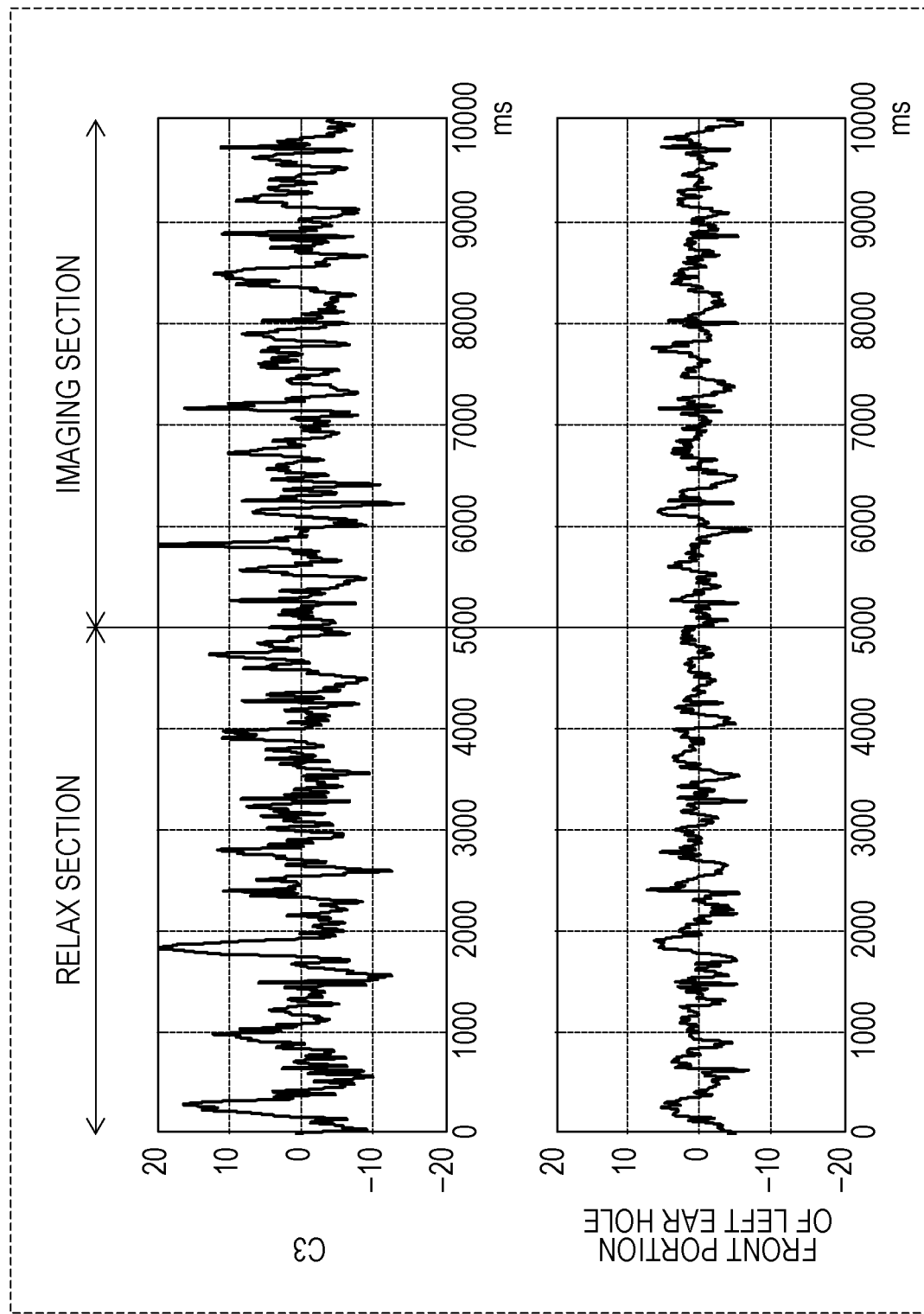
FIG. 5 is a diagram illustrating, as an example of brain waveforms in measurement, a voltage waveform between an electrode at a certain position and a reference electrode and a voltage waveform between an electrode in a front portion of a left ear hole and the reference electrode under a right-hand condition.

FIG. 5 illustrates, as an example of brain waveforms in measurement, a voltage waveform between the electrode at the position C3 and the reference electrode and a voltage waveform between the electrode in the front portion of the left ear hole and the reference electrode under the right-hand condition. FIG. 5 illustrates voltage waveforms in a relax section and an imaging section following the relax section. Compared to the amplitude of the voltage waveform between the electrode at the position C3 and the reference electrode, the amplitude of the voltage waveform between the electrode in the front portion of the left ear hole and the reference electrode is small. As a whole, the voltage waveform between the electrode at the position C3 and the reference electrode is similar to the voltage waveform between the electrode in the front portion of the left ear hole and the reference electrode.

Figure 6:
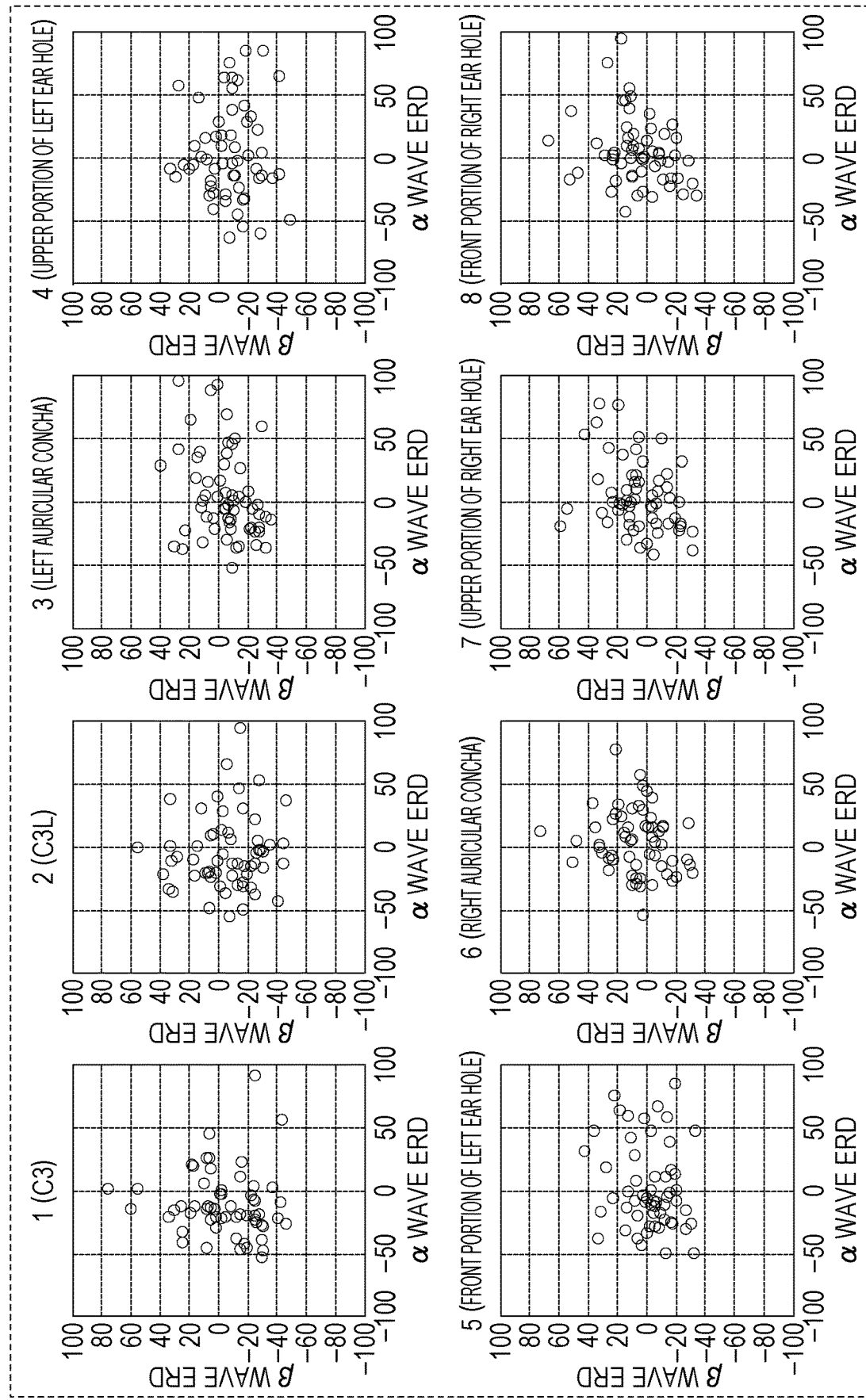
FIG. 6 illustrates, as an example of experiment results, the ERD change rates in the $\alpha$ waveband and the ERD change rates in the $\beta$ waveband in individual trials for individual measurement electrodes, calculated from the voltages between the individual measurement electrodes and the reference electrode under the right-hand condition.

FIG. 6 illustrates, as an example of experiment results, the ERD change rates in the $\alpha$ waveband and the ERD change rates in the $\beta$ waveband in individual trials for individual measurement electrodes, calculated from the voltages between the individual measurement electrodes and the reference electrode under the right-hand condition. The number of trials is 60 (60 processes). In FIG. 6, the number of the measurement electrode (electrode position) is indicated on the upper side of each graph.

Figure 7:
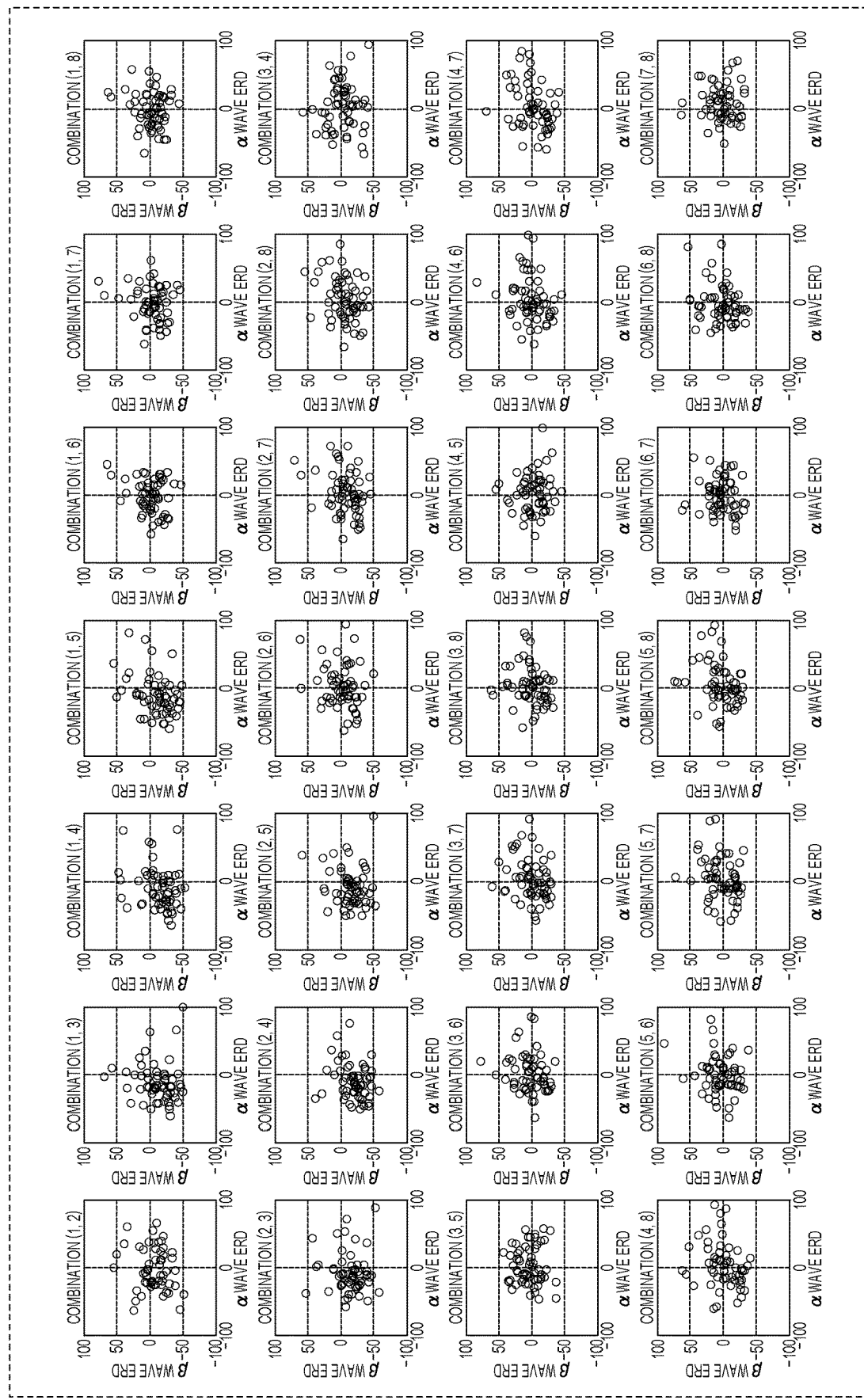
FIG. 7 illustrates the ERD change rates in the $\alpha$ waveband and the ERD change rates in the $\beta$ waveband calculated from the voltages between measurement electrodes in individual combinations of two different measurement electrodes under the right-hand condition.

FIG. 7 illustrates the ERD change rates in the $\alpha$ waveband and the ERD change rates in the $\beta$ waveband calculated from the voltages between measurement electrodes in individual combinations of two different measurement electrodes (the number of combinations is 28) under the right-hand condition. Each graph includes the ERD change rates in 60 trials (60 processes). In FIG. 7, the number of a combination of measurement electrodes is indicated on the upper side of each graph. The horizontal axis represents the ERD change rate in the $\alpha$ waveband and the vertical axis represents the ERD change rate in the $\beta$ waveband. In the horizontal or vertical axis, if the change rate is lower than zero, it can be determined that ERD was detected.

As can be understood from FIGS. 6 and 7, the test subject of the ERD measurement experiments conducted by the inventors has a higher ERD change rate in the $\beta$ waveband than in the $\alpha$ waveband. However, this is an example. It is known that ERD occurs in either or both of the $\alpha$ waveband and the $\beta$ waveband depending on a test subject.

Figure 8:
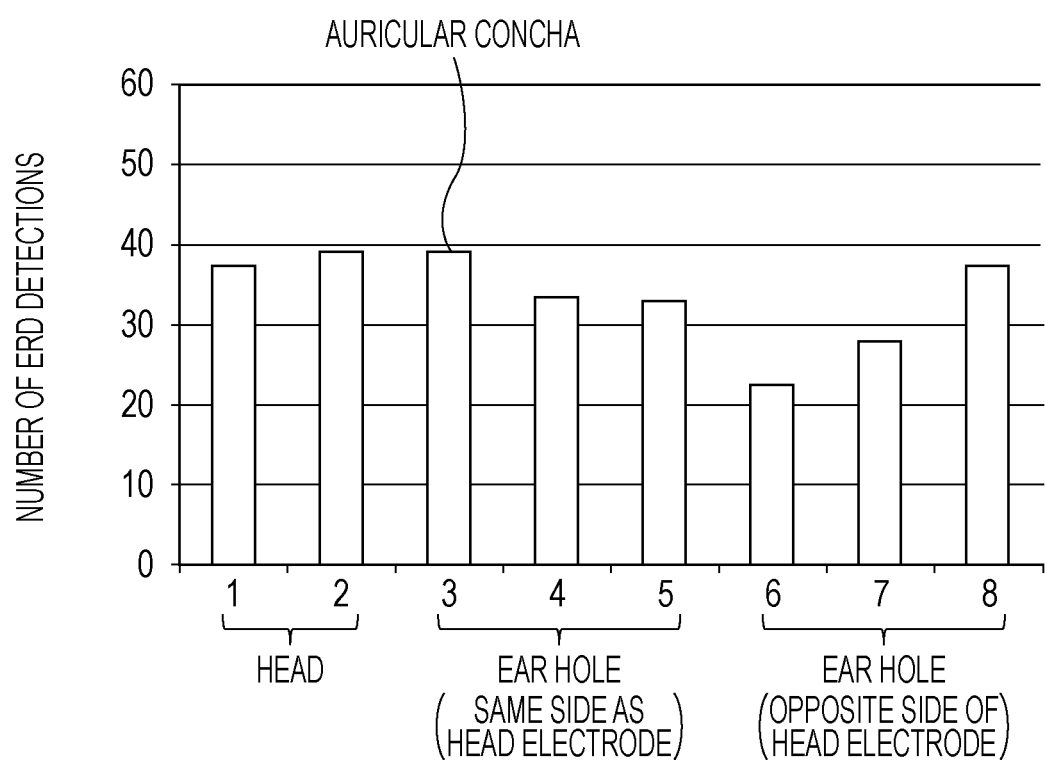
FIG. 8 is a diagram illustrating the number of ERD detections (an average value in the right-hand condition and left-hand condition) in which it is determined that ERD exists in an imaging section on the basis of ERD change rates in the $\beta$ waveband calculated from potentials between the reference electrode and the individual measurement electrodes.

In FIG. 8, the vertical axis represents an average value of the number of ERD detections under the right-hand condition and the number of ERD detections under the left-hand condition, and the numbers along the horizontal axis represent the electrode numbers illustrated in FIG. 4.

The number of ERD detections under the right-hand condition is the number of detections in which the individual electrodes are attached to the test subject in accordance with the right-hand condition illustrated in FIG. 4 and it is determined that ERD exists in the imaging section on the basis of the ERD change rates in the $\beta$ waveband calculated from the voltages between the individual measurement electrodes and the reference electrode.

The number of ERD detections under the left-hand condition is the number of detections in which the individual electrodes are attached to the test subject in accordance with the left-hand condition illustrated in FIG. 4 and it is determined that ERD exists in the imaging section on the basis of the ERD change rates in the $\beta$ waveband calculated from the voltages between the individual measurement electrodes and the reference electrode.

The numbers of ERD detections calculated from the voltages between the head electrodes and the reference electrode are 30 or more. The numbers of ERD detections calculated from the voltages between the ear hole electrodes located in the ear hole on the same side of the body as the head electrodes and the reference electrode located on the mastoid on the same side of the body as the head electrodes are 30 or more. In particular, the number of ERD detections calculated from the voltage between the electrode located on the auricular concha and the reference electrode is the largest.

As illustrated in FIG. 4, in the ERD detection experiments conducted by the inventors, the head electrodes and the reference electrode were located on the side of the body opposite to the side having a movement imaging hand. For example, under the right-hand condition, the head electrodes were located in the left portion of the head and the reference electrode was located on the left mastoid.

From the result of these experiments indicating that the number of ERD detections calculated from the voltage between an electrode located at a position included in the ear hole of the ear on the same side of the body as the side provided with the head electrodes, for example, an ear hole electrode located on the auricular concha, and the reference electrode located on the mastoid on the same side of the body as the side provided with the head electrodes (the ear and mastoid on the side of the body opposite to the side having a movement imaging hand) is almost the same as the number of ERD detections calculated from the voltage between the head electrode and the reference electrode, it has become clear that ERD can be detected with almost the same accuracy as in the case of locating electrodes on the head, by locating a reference electrode on the mastoid on the side of the body opposite to the side having a movement imaging hand and locating a measurement electrode at a position included in the ear hole, for example, the auricular concha, on the side of the body opposite to the side having the movement imaging hand.

In a measurement in which a reference electrode is located on a mastoid and a measurement electrode is located in an ear hole, it is not necessary to attach an electrode on the head, where it is not easy to attach an electrode due to the hair, and thus ERD measurement can be performed much more easily.

Figure 9:
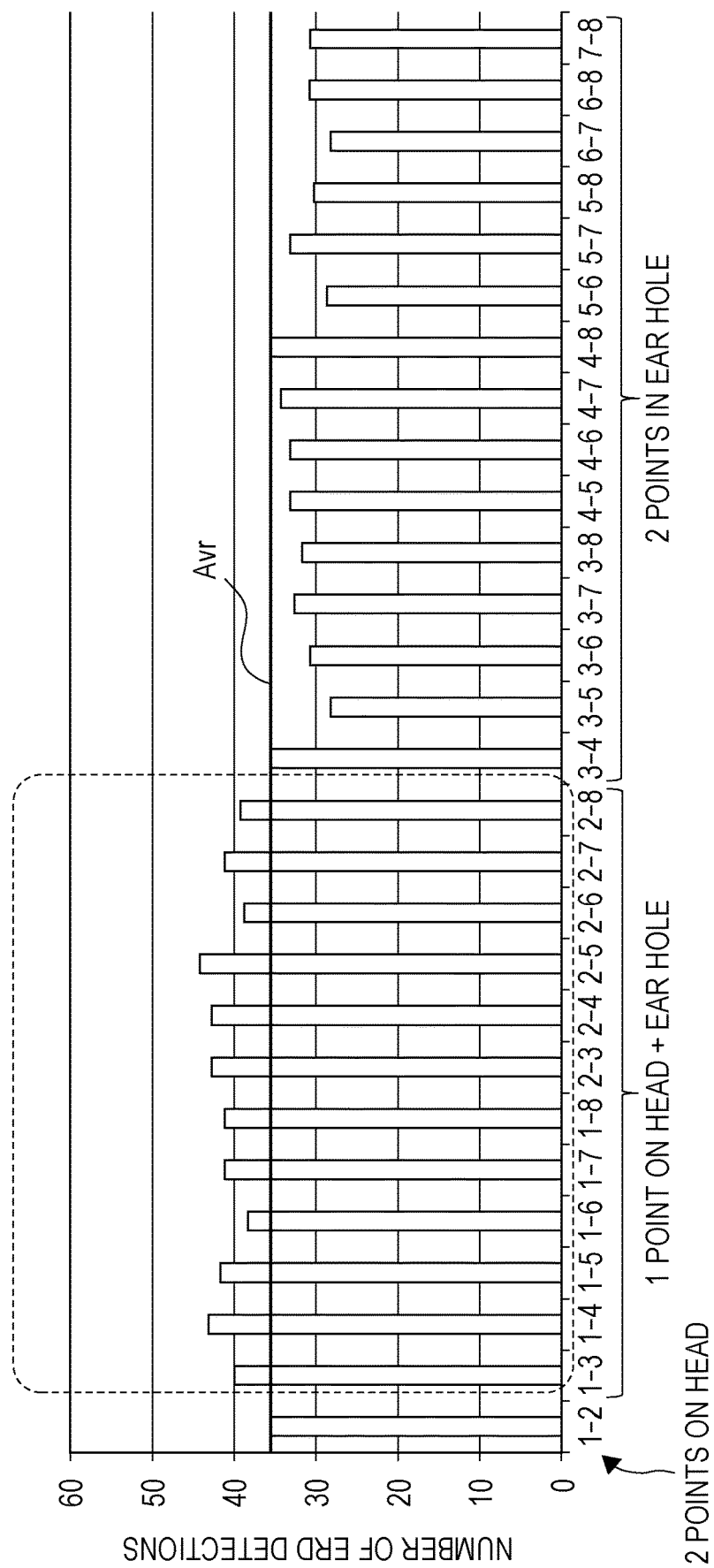
FIG. 9 is a diagram illustrating the number of ERD detections (an average value in the right-hand condition and left-hand condition) Avr in which it is determined that ERD exists on the basis of ERD change rates in the $\beta$ waveband calculated from differential waveforms of combinations of the individual measurement electrodes.

In FIG. 9, the vertical axis represents an average value of the number of ERD detections under the right-hand condition and the number of ERD detections under the left-hand condition. The combinations of numbers along the horizontal axis of FIG. 9 are combinations of two different electrode numbers illustrated in FIG. 4. For example, 1-2 represents a combination of the electrode number 1 (the position C3 in the right-hand condition) and the electrode number 2 (the position C3L in the right-hand condition).

The number of ERD detections under the right-hand condition is the number of detections in which the individual electrodes are attached to the test subject in accordance with the right-hand condition illustrated in FIG. 4 and it is determined that ERD exists in the imaging section on the basis of the ERD change rate in the $\beta$ waveband calculated from the voltage between the two measurement electrodes.

The number of ERD detections under the left-hand condition is the number of detections in which the individual electrodes are attached to the test subject in accordance with the left-hand condition illustrated in FIG. 4 and it is determined that ERD exists in the imaging section on the basis of the ERD change rate in the $\beta$ waveband calculated from the voltage between the two measurement electrodes.

In FIG. 9, Avr represents an average value of the number of ERD detections in the $\beta$ waveband calculated from the voltage between the electrode having the electrode number 1 (the electrode at the position C3) and the electrode having the electrode number 2 (the electrode at the position C3L) under the right-hand condition, and the number of ERD detections in the $\beta$ waveband calculated from the voltage between the electrode having the electrode number 1 (the electrode at the position C4) and the electrode having the electrode number 2 (the electrode at the position C4L) under the left-hand condition. As illustrated in FIG. 9, the number of ERD detections calculated from the voltage between the head electrode and the ear hole electrode in every combination of one head electrode and one ear hole electrode (12 combinations represented by labels 1-3 to 2-8) is larger than Avr, which represents the number of ERD detections calculated from the voltage between the two head electrodes (label 1-2).

As described above, it has become clear, through the experiments conducted by the inventors, that the number of ERD detections is larger in the case of using an electrode located at one point around the motor area of the head portion on the side of the body opposite to the side having a movement imaging hand and an electrode located at one point in the ear hole on the side of the body opposite to the side having the movement imaging hand, than in the case of using two electrodes located around the motor area of the head portion on the side of the body opposite to the side having the movement imaging hand. As a result of optimizing electrode locations, a motor intention of a user can be detected with higher accuracy by using ERD as an index.

The outline of embodiments of the present disclosure is as follows.

A determination system according to an embodiment of the present disclosure includes a head electrode that is located on a left head portion of a user when an intention of the user to move a portion on a right side of a body of the user is detected and that is located on a right head portion of the user when an intention of the user to move a portion on a left side of the body of the user is detected; an ear hole electrode that is located in an ear hole of the user; an electroencephalogram signal measurer that obtains a voltage between the head electrode and the ear hole electrode; and a determiner that determines whether or not a change in the voltage includes the intention of the user to move the portion on the right side of the body of the user or the intention of the user to move the portion on the left side of the body of the user.

In a case where the change in the voltage is a first threshold or larger, the determiner may determine that the change in the voltage includes the intention of the user to move the portion on the right side of the body of the user or the intention of the user to move the portion on the left side of the body of the user.

The ear hole of the user may include an auricular concha or an external auditory canal.

The determination system may further include an indicator that indicates, to the user, a first time section in which the user has a motor intention and a second time section in which the user does not have a motor intention. In a case where a strength of the voltage in a certain frequency band in the first time section is smaller than a strength of the voltage in the certain frequency band in the second time section, the determiner may determine that there is the intention of the user to move the portion on the right side of the body of the user or the intention of the user to move the portion on the left side of the body of the user.

When the intention of the user to move the portion on the right side of the body of the user is detected, the head electrode may be located on the left head portion of the user and the ear hole electrode may be located in a right ear hole. When he intention of the user to move the portion on the left side of the body of the user is detected, the head electrode may be located on the right head portion of the user and the ear hole electrode may be located in a left ear hole.

When the intention of the user to move the portion on the right side of the body of the user is detected, the head electrode may be located on the left head portion of the user, the ear hole electrode may be located in a left ear hole, and a reference electrode may be located on a left mastoid of the user. When the intention of the user to move the portion on the left side of the body of the user is detected, the head electrode may be located on the right head portion of the user, the ear hole electrode may be located in a right ear hole, and the reference electrode may be located on a right mastoid of the user.

A control signal output system according to another embodiment of the present disclosure outputs a control signal for controlling an operation of a rehabilitation assistance apparatus including an attachment that is attached to a user and assists movement of the user and an actuator that operates the attachment. The control signal output system includes a head electrode that is located on a left head portion of the user when a right side of a body of the user is rehabilitated and that is located on a right head portion of the user when a left side of the body of the user is rehabilitated; an ear hole electrode that is located in an ear hole of the user; an electroencephalogram signal measurer that obtains a voltage between the head electrode and the ear hole electrode; and a signal outputter that outputs the control signal for operating the actuator in accordance with a change in the voltage.

In a case where the change in the voltage is a first threshold or larger, the signal outputter may output the control signal for operating the actuator.

The ear hole of the user may include an auricular concha or an external auditory canal.

The control signal output system may further include an indicator that indicates, to the user, a first time section in which the user has a motor intention and a second time section in which the user does not have a motor intention. In a case where a strength of the voltage in a certain frequency band in the first time section is smaller than a strength of the voltage in the certain frequency band in the second time section, the signal outputter may output the control signal for operating the actuator.

A rehabilitation system according to still another embodiment of the present disclosure includes an attachment that is attached to a user and assists movement of the user; an actuator that operates the attachment; a head electrode that is located on a left head portion of the user when a right side of a body of the user is rehabilitated and that is located on a right head portion of the user when a left side of the body of the user is rehabilitated; an ear hole electrode that is located in an ear hole of the user; an electroencephalogram signal measurer that obtains a voltage between the head electrode and the ear hole electrode; and a signal outputter that outputs a control signal for operating the actuator in accordance with a change in the voltage.

In a case where the change in the voltage is a first threshold or larger, the signal outputter may output the control signal for operating the actuator.

The ear hole of the user may include an auricular concha or an external auditory canal.

The rehabilitation system may further include an indicator that indicates, to the user, a first time section in which the user has a motor intention and a second time section in which the user does not have a motor intention. In a case where a strength of the voltage in a certain frequency band in the first time section is smaller, by a second threshold or larger, than a strength of the voltage in the certain frequency band in the second time section, the signal outputter may output the control signal for operating the actuator.

A determination method according to still another embodiment of the present disclosure includes obtaining a voltage between a head electrode and an ear hole electrode by using the head electrode and the ear hole electrode, the head electrode being located on a left head portion of a user when an intention of the user to move a portion on a right side of a body of the user is detected and located on a right head portion of the user when an intention of the user to move a portion on a left side of the body of the user is detected, the ear hole electrode being located in an ear hole of the user; and determining whether or not a change in the voltage includes the intention of the user to move the portion on the right side of the body of the user or the intention of the user to move the portion on the left side of the body of the user.

A control signal output method according to still another embodiment of the present disclosure is a control signal output method for outputting a control signal for controlling an operation of a rehabilitation assistance apparatus including an attachment that is attached to a user and assists movement of the user and an actuator that operates the attachment. The method includes obtaining a voltage between a head electrode and an ear hole electrode by using the head electrode and the ear hole electrode, the head electrode being located on a left head portion of the user when an intention of the user to move a portion on a right side of a body of the user is detected and located on a right head portion of the user when an intention of the user to move a portion on a left side of the body of the user is detected, the ear hole electrode being located in an ear hole of the user; and outputting the control signal for operating the actuator in accordance with a change in the voltage.

A recording medium according to still another embodiment of the present disclosure is a recording medium storing a computer program that causes a computer to perform processing. The recording medium is non-volatile and computer-readable. The processing includes obtaining a voltage between a head electrode and an ear hole electrode by using the head electrode and the ear hole electrode, the head electrode being located on a left head portion of a user when an intention of the user to move a portion on a right side of a body of the user is detected and located on a right head portion of the user when an intention of the user to move a portion on a left side of the body of the user is detected, the ear hole electrode being located in an ear hole of the user; and determining whether or not a change in the voltage includes the intention of the user to move the portion on the right side of the body of the user or the intention of the user to move the portion on the left side of the body of the user.

A recording medium according to still another embodiment of the present disclosure is a recording medium storing a computer program that causes a computer to perform processing of outputting a control signal for controlling an operation of a rehabilitation assistance apparatus including an attachment that is attached to a user and assists movement of the user and an actuator that operates the attachment. The recording medium is non-volatile and computer-readable. The processing includes obtaining a voltage between a head electrode and an ear hole electrode by using the head electrode and the ear hole electrode, the head electrode being located on a left head portion of the user when an intention of the user to move a portion on a right side of a body of the user is detected and located on a right head portion of the user when an intention of the user to move a portion on a left side of the body of the user is detected, the ear hole electrode being located in an ear hole of the user; and outputting the control signal for operating the actuator in accordance with a change in the voltage.

Hereinafter, an EEG signal acquisition system according to an exemplary embodiment of the present disclosure will be described. An ERD measurement system will be described as an example of the EEG signal acquisition system. After that, a control signal output system and a rehabilitation system will be described as a modification example of the ERD measurement system.

Embodiment

First, the outline of the ERD measurement system will be described. After that, the configuration and operation of the ERD measurement system including an ERD measurement apparatus will be described.

Figure 10:
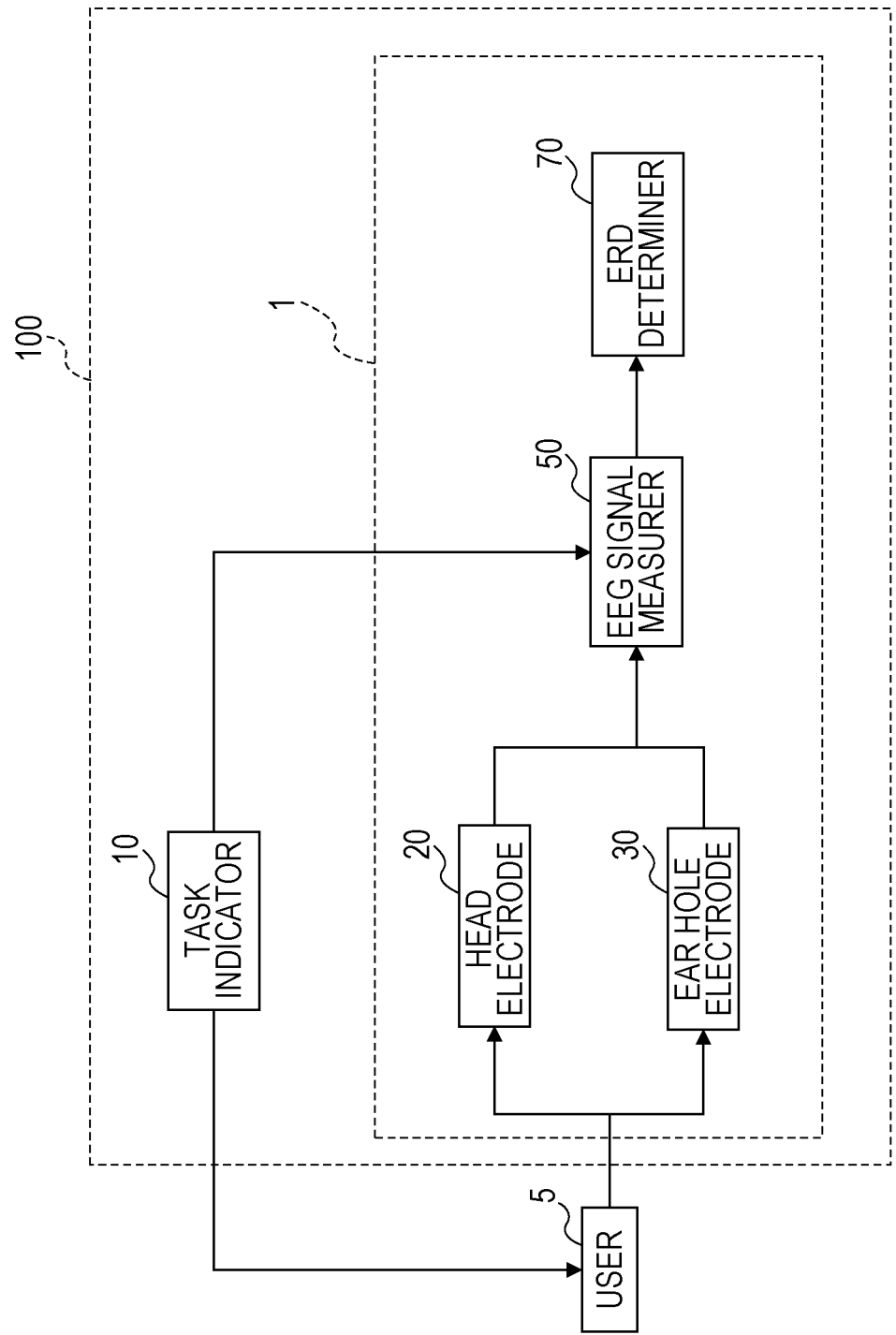
FIG. 10 is a configuration diagram illustrating functional blocks of an ERD measurement system according to an exemplary embodiment.

FIG. 10 illustrates the configuration of the functional blocks of an ERD measurement system 100 according to the embodiment. The ERD measurement system 100 includes a task indicator 10 and an ERD measurement apparatus 1. The ERD measurement apparatus 1 includes a head electrode 20, an ear hole electrode 30, an EEG signal measurer 50, and an ERD determiner 70. The ERD measurement apparatus 1 is connected to the task indicator 10 in a wired or wireless manner.

Task Indicator 10

The task indicator 10 is, for example, a tablet terminal. The task indicator 10 is capable of indicating, for example, a text or image message to a user 5 via a display panel, such as a liquid crystal panel. Alternatively, the task indicator 10 is capable of indicating a voice message to the user 5 via a speaker. More specifically, the task indicator 10 indicates a switch timing between a relax section and a movement imaging section to the user 5 by using an image and/or voice. The time period of each of the relax section and the movement imaging section may be, for example, five seconds.

The task indicator 10 transmits, to the EEG signal measurer 50, section information indicating whether a current section is a relax section or a movement imaging section. The task indicator 10 may notify the EEG signal measurer 50 of a switch timing between a relax section and a movement imaging section. Which of a relax section and a movement imaging section is to be started first may be predetermined.

In the embodiment, the ERD measurement system 100 includes the task indicator 10, but it is not necessary for the ERD measurement system 100 to include the task indicator 10. For example, it is assumed that the user 5 introduces the ERD measurement apparatus 1 under a situation where the user 5 personally owns a tablet terminal. In this case, it can be said that the ERD measurement apparatus 1 is manufactured and sold as the ERD measurement system 100. The tablet terminal owned by the user 5 can function as the task indicator 10 that indicates the above-described switch timing.

Head Electrode 20

The head electrode 20 is an electrode that is located on the head of the user 5 and measures brain waves of the user 5. In the case of detecting a motor intention to move a portion on the right side of the body of the user 5, the head electrode 20 is located on a head portion on the left side (a head portion on the left side of the body). In the case of detecting a motor intention to move a portion on the left side of the body of the user 5, the head electrode 20 is located on a head portion on the right side (a head portion on the right side of the body). An example of a portion on the right side of the body of the user 5 is the right hand or the right foot. It is known that ERD is a component reflecting a motor intention and thus occurs regardless of a portion that is to be moved. An example of a portion on the left side of the body of the user 5 is the left hand or the left foot.

A motor intention of the right side of the body of the user 5 means, for example, an intention of the user 5 to move the right hand or the right foot. A motor intention of the left side of the body of the user 5 means, for example, an intention of the user 5 to move the left hand or the left foot. A motor intention of the right hand of the user 5 means an intention of the user 5 to move the right hand, a motor intention of the right foot of the user 5 means an intention of the user 5 to move the right foot, a motor intention of the left hand of the user 5 means an intention of the user 5 to move the left hand, and a motor intention of the left foot of the user 5 means an intention of the user 5 to move the left foot.

In the case of rehabilitating the right side of the body of the user 5, the head electrode 20 is located on the head portion on the left side. In the case of rehabilitating the left side of the body of the user 5, the head electrode 20 is located on the head portion on the right side. In the case of rehabilitating the right hand or the right foot of the user 5, the head electrode 20 is located on the head portion on the left side of the body. In the case of rehabilitating the left hand or the left foot of the user 5, the head electrode 20 is located on the head portion of the right side of the body.

For example, in the case of detecting an intention of the user 5 to extend a right finger of the user 5, an electrode is located within a certain radius around the position C3 in the international 10-20 system. For example, in the case of detecting an intention of the user 5 to extend a left finger of the user 5, an electrode is located within a certain radius around the position C4 in the international 10-20 system. The certain radius is, for example, 30 mm or less.

Ear Hole Electrode 30

The ear hole electrode 30 is an electrode that is located in an ear hole of the user 5 and measures brain waves of the user 5. Desirably, the ear hole electrode 30 is located along a first curve of the ear hole of the user 5 so that the ear hole electrode 30 is easily brought into contact with the user 5 and ERD can be detected with high accuracy. The first curve is included in an external auditory canal. As described above, each of the ear hole electrodes E illustrated in FIG. 3A or 3B is an example of the ear hole electrode 30. The ear hole electrode 30 may include, in addition to an electrode, an operation amplifier circuit or the like for measuring a potential difference V2 between the ear hole electrode and the reference electrode.

In the case of detecting a motor intention of the right hand or right foot of the user 5, the ear hole electrode 30 may be located in either of the right ear hole or left ear hole. In the case of detecting a motor intention of the left hand or left foot of the user 5, the ear hole electrode 30 may be located in either of the right ear hole or left ear hole.

In the case of rehabilitating the right side of the body of the user 5, the ear hole electrode 30 may be located in either of the right ear hole or left ear hole. In the case of rehabilitating the left side of the body of the user 5, the ear hole electrode 30 may be located in either of the right ear hole or left ear hole. The ear hole electrode 30 may be located inside the external auditory canal.

To record brain waves of the user 5, the ear hole electrode 30 desirably comes into contact with the user 5 with a certain pressure or more being applied to the ear hole electrode 30. For this purpose, the ear hole electrode 30 may be provided in an ear mold made by taking a cast of an ear of the user 5 in advance. The ear hole electrode 30 may be provided in a general-purpose ear chip without taking a cast of the ear.

Regarding the locations of the head electrode 20 and the ear hole electrode 30, it has been found through the trials executed by the inventors that the following combinations are preferable because ERD occurs in the motor area of the head portion on the opposite side of a movement hand. No significant effects were seen in the trial results in a case where a reference electrode was located on a right mastoid and a case where a reference electrode was located on a left mastoid.

(1) Preferable electrode positions in the case of imaging extension of right fingers:

Left head portion and right ear hole, the reference electrode position is the left mastoid or Left head portion and right ear hole, the reference electrode position is the right mastoid (2) More preferable electrode positions in the case of imaging extension of right fingers:

Left head portion and left ear hole, the reference electrode position is the left mastoid or Left head portion and left ear hole, the reference electrode position is the right mastoid (3) Preferable electrode positions in the case of imaging extension of left fingers:

Right head portion and left ear hole, the reference electrode position is the left mastoid or Right head portion and left ear hole, the reference electrode position is the right mastoid (4) More preferable electrode positions in the case of imaging extension of left fingers:

Right head portion and right ear hole, the reference electrode position is the left mastoid or Right head portion and right ear hole, the reference electrode position is the right mastoid V1 represents the potential difference between the head electrode 20 and the reference electrode, and V2 represents the potential difference between the ear hole electrode 30 and the reference electrode. In FIG. 10, the illustration of the reference electrode is omitted.

EEG Signal Measurer 50

The EEG signal measurer 50 measures, as an EEG signal of the user 5, a potential difference between the head electrode 20 and the ear hole electrode 30. The EEG signal measurer 50 may include a bioamplifier that amplifies a potential difference between the head electrode 20 and the ear hole electrode 30.

The EEG signal measurer 50 receives, from the task indicator 10, section information indicating whether a current section is a relax section or a movement imaging section and a potential difference between the head electrode 20 and the ear hole electrode 30 (EEG signal). Accordingly, the EEG signal measurer 50 determines whether the received EEG signal is an EEG signal of the user 5 in the relax section or an EEG signal of the user 5 in the movement imaging section.

The movement imaging section means a time section in which the user 5 has a motor intention to move the right hand, right foot, left hand, or left foot. The relax section means a time section in which the user 5 does not have a motor intention to move the right hand, right foot, left hand, or left foot.

Further, the EEG signal measurer 50 may hold in advance, in a storage unit such as a memory, buffer, register, or the like (not illustrated), information representing the time periods for a movement imaging section and a relax section (time information) of the user 5. The EEG signal measurer 50 may obtain an EEG signal of the user 5 in the relax section and an EEG signal of the user 5 in the movement imaging section with reference to the time information about the movement imaging section and the relax section in the storage unit.

ERD Determiner 70

The ERD determiner 70 determines, by using a measured EEG signal (a potential difference between the head electrode 20 and the ear hole electrode 30), whether or not there is a motor intention to move the right hand or right foot of the user 5 or the left hand or left foot of the user 5.

If the ERD determiner 70 detects a time change in a signal strength (a voltage change value) of a first threshold or larger in the measured EEG signal, the ERD determiner 70 determines that there is a motor intention to move the right hand or right foot of the user 5 or the left hand or left foot of the user 5. For example, if the difference between the strength of the EEG signal in the movement imaging section (second voltage value) and the strength of the EEG signal in the relax section (first voltage value) is a value equal to or larger than the first threshold, the ERD determiner 70 determines that there is a motor intention to move the right hand or right foot of the user 5 or the left hand or left foot of the user 5. In other words, if {(first voltage value)−(second voltage value)}≥ (first threshold), the ERD determiner 70 determines that there is a motor intention to move the right hand or right foot of the user 5 or the left hand or left foot of the user 5.

Further, the ERD determiner 70 performs frequency analysis on an EEG signal of the user 5 measured by the EEG signal measurer 50. As described above, the frequency band in which ERD occurs varies among users. For example, ERD may occur in the β waveband in the user 5, whereas ERD may occur both in the α waveband and the β waveband in another user. Frequency analysis is performed for each of the relax section and the movement imaging section. If a certain frequency band power (voltage strength) is smaller in the movement imaging section than in the relax section, the ERD determiner 70 determines that ERD exists.

An example of a certain frequency band is the α waveband ranging from 8 to 12 Hz, the β waveband ranging from 13 to 25 Hz, or both of the α waveband and β waveband ranging from 8 to 25 Hz. The certain frequency band may be set to a frequency band around the α waveband and around the β waveband in accordance with the characteristic of the brain waves of the user 5.

Hereinafter, the ERD determiner 70 is also referred to as a determiner.

Before describing the operation of the ERD measurement system 100, a description will be given of an environment in which the ERD measurement system 100 is used.

Usage Environment

Figure 11:
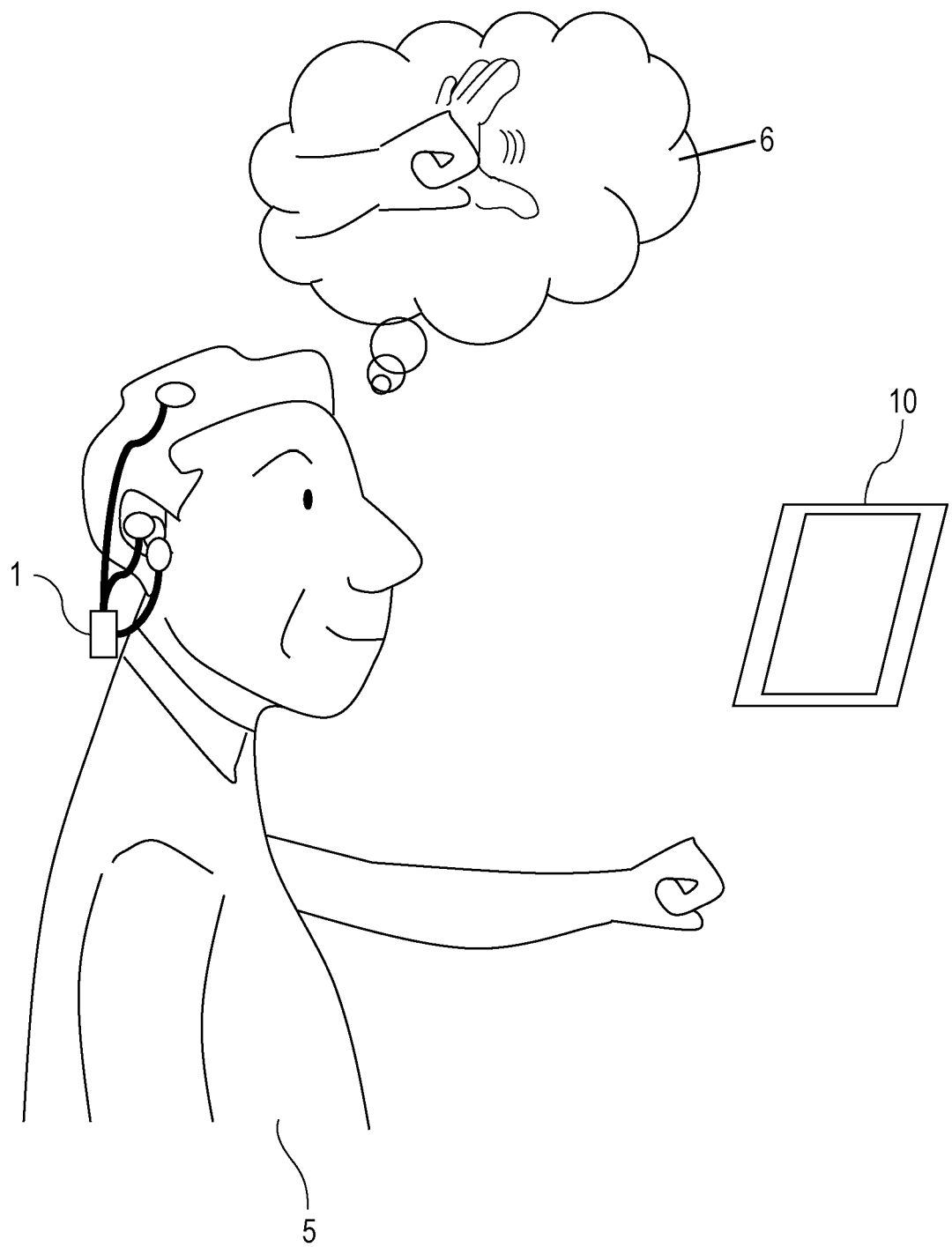
FIG. 11 is a diagram illustrating the configuration of the ERD measurement system and an environment in which the system is used according to an exemplary embodiment.

FIG. 11 illustrates the configuration of the ERD measurement system 100 according to the embodiment and an environment in which the ERD measurement system 100 is used. FIG. 11 includes a thought bubble 6 that is a representation of a motor intention of the user 5.

The task indicator 10 indicates a switch timing between a relax section and a movement imaging section to the user 5. The time period of each of the relax section and the movement imaging section may be, for example, five seconds.

In the relax section, the task indicator 10 indicates a message, for example, "please relax". Alternatively, the task indicator 10 may simply indicate characters (a word) "relax". The task indicator 10 transmits information specifying the timing of the relax section to the EEG signal measurer 50 of the ERD measurement apparatus 1 (see FIG. 10).

The EEG signal measurer 50 of the ERD measurement apparatus 1 receives the information specifying the relax section from the task indicator 10. Subsequently, the ERD determiner 70 of the ERD measurement apparatus 1 performs frequency analysis on the brain waves of the user 5 in the relax section.

In the movement imaging section, the task indicator 10 indicates a message, for example, "please image opening up your hand". Alternatively, the task indicator 10 may simply indicate characters (a word) "image". The task indicator 10 transmits information specifying the movement imaging section to the EEG signal measurer 50 of the ERD measurement apparatus 1 (see FIG. 10).

The EEG signal measurer 50 of the ERD measurement apparatus 1 receives the information specifying the movement imaging section from the task indicator 10. Subsequently, the ERD determiner 70 of the ERD measurement apparatus 1 performs frequency analysis on the brain waves of the user 5 in the movement imaging section.

Processing Performed by ERD Measurement System 100

Figure 12:
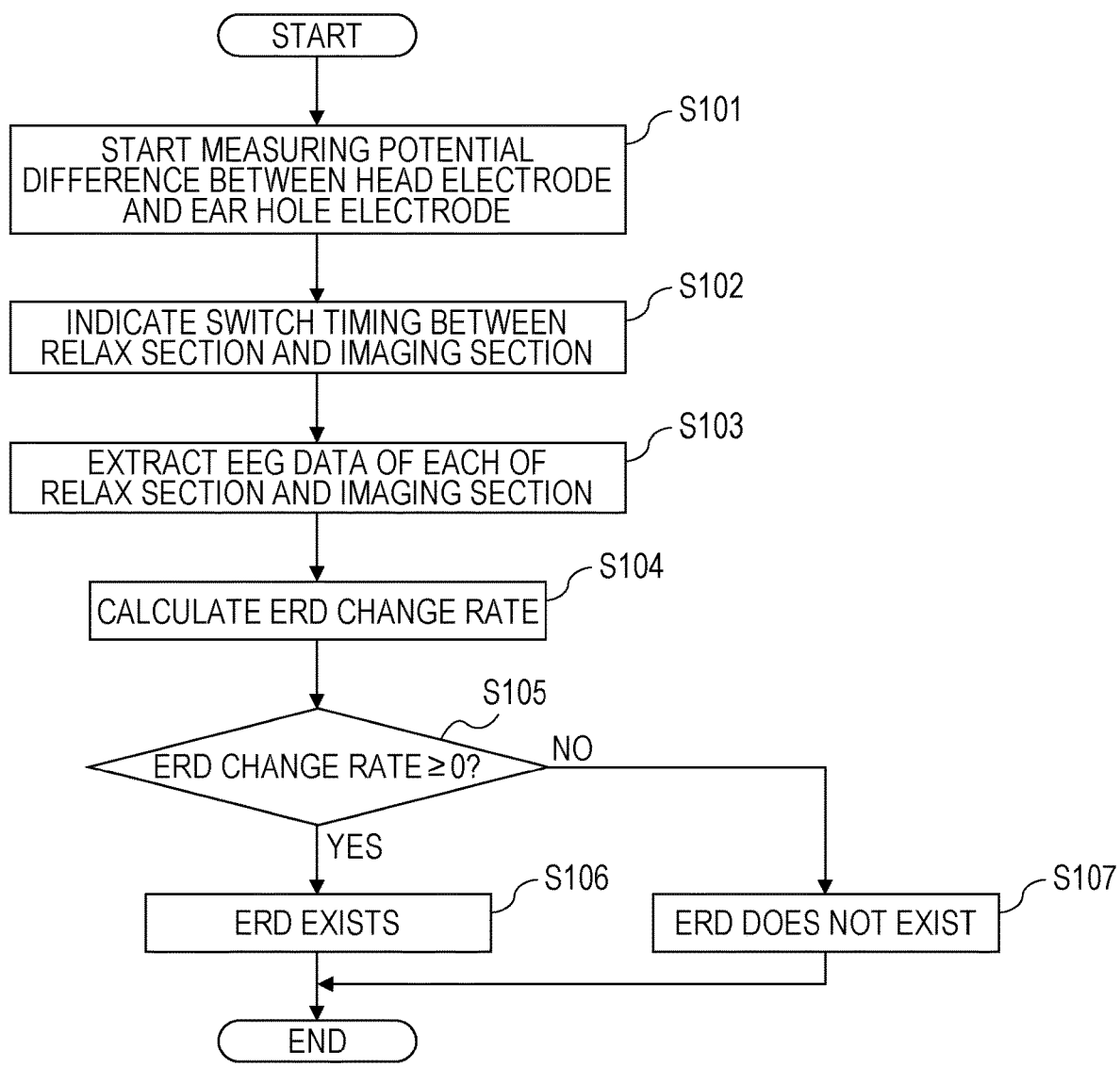
FIG. 12 is a flowchart illustrating a procedure of processing performed by the ERD measurement system.

Next, a procedure of processing performed by the ERD measurement system 100 illustrated in FIG. 10 will be described with reference to FIG. 12. FIG. 12 is a flowchart illustrating the procedure of the processing performed by the ERD measurement system 100.

In step S101, the EEG signal measurer 50 starts measuring the potential difference between the head electrode 20 and the ear hole electrode 30 of the user 5 and holds data of the potential difference corresponding to a necessary time period or more.

In step S102, the task indicator 10 indicates a switch timing between a relax section and a movement imaging section to the user 5. The time period of each of the relax section and the movement imaging section may be, for example, five seconds. The task indicator 10 may indicate a message "please relax" in the relax section and may indicate a message "please image opening up your hand" in the movement imaging section. Alternatively, the task indicator 10 may simply indicate a message by using characters (a word) "relax" in the relax section and may simply indicate a message by using characters (a word) "image" in the movement imaging section. Subsequently, the task indicator 10 transmits, to the EEG signal measurer 50, information specifying the relax section, a label indicating the relax section, information specifying the movement imaging section, and a label indicating the movement imaging section.

In step S103, on the basis of the information specifying the relax section, the label indicating the relax section, the information specifying the movement imaging section, and the label indicating the movement imaging section obtained from the task indicator 10 in step S102, the EEG signal measurer 50 extracts EEG data of the user 5 obtained through the measurement for each of the relax section and the movement imaging section. Subsequently, the EEG signal measurer 50 transmits, to the ERD determiner 70, the extracted EEG data of the user 5 in the relax section, the label indicating the relax section, the extracted EEG data of the user 5 in the movement imaging section, and the label indicating the movement imaging section.

In step S104, the ERD determiner 70 performs frequency analysis on the EEG data in the relax section and the EEG data in the movement imaging section received from the EEG signal measurer 50. Subsequently, the ERD determiner 70 calculates an ERD change rate by using, for example, the above-described ERD change rate in the α waveband $(Pr\alpha-Pi\alpha)/Pr\alpha \times 100$ or ERD change rate in the β waveband $(Pr\beta-Pi\beta)/Pr\beta \times 100$ on the basis of the voltage strength in the certain frequency band of the brain waves for the series of relax section and movement imaging section.

In step S105, the ERD determiner 70 determines whether or not the ERD change rate calculated in step S104 is equal to or higher than a predetermined threshold. In this embodiment, the predetermined threshold is 0. That is, the ERD determiner 70 performs the processing in step S106 if the ERD change rate is a positive value or zero, and performs the processing in step S107 if the ERD change rate is a negative value.

In step S106, the ERD determiner 70 determines that ERD exists. This means that the brain waves of the user 5 include a motor intention related to the right hand, right foot, left hand, or left foot of the user 5.

In step S107, the ERD determiner 70 determines that ERD does not exist. This means that the brain waves of the user 5 do not include a motor intention related to the right hand, right foot, left hand, or left foot of the user 5.

The ERD measurement system 100 according to this embodiment calculates a voltage strength in a certain frequency band in a differential waveform (change in voltage) of brain waves between one head electrode located around the motor area of the head portion on the side of the body opposite to the side having a movement imaging hand of a user and one ear hole electrode located in the ear hole on the side of the body opposite to the side having the movement imaging hand of the user. If the voltage strength in the certain frequency band in a relax section is larger than the voltage strength in the certain frequency band in a movement imaging section, it is determined that ERD exists. Accordingly, a motor intention of the user can be detected with high accuracy by using ERD as an index.

The ERD measurement system 100 has been described above as an example of an EEG signal acquisition system.

Next, a control signal output system and a rehabilitation system including the control signal output system will be described with reference to FIGS. 13 to 15.

Figure 13:
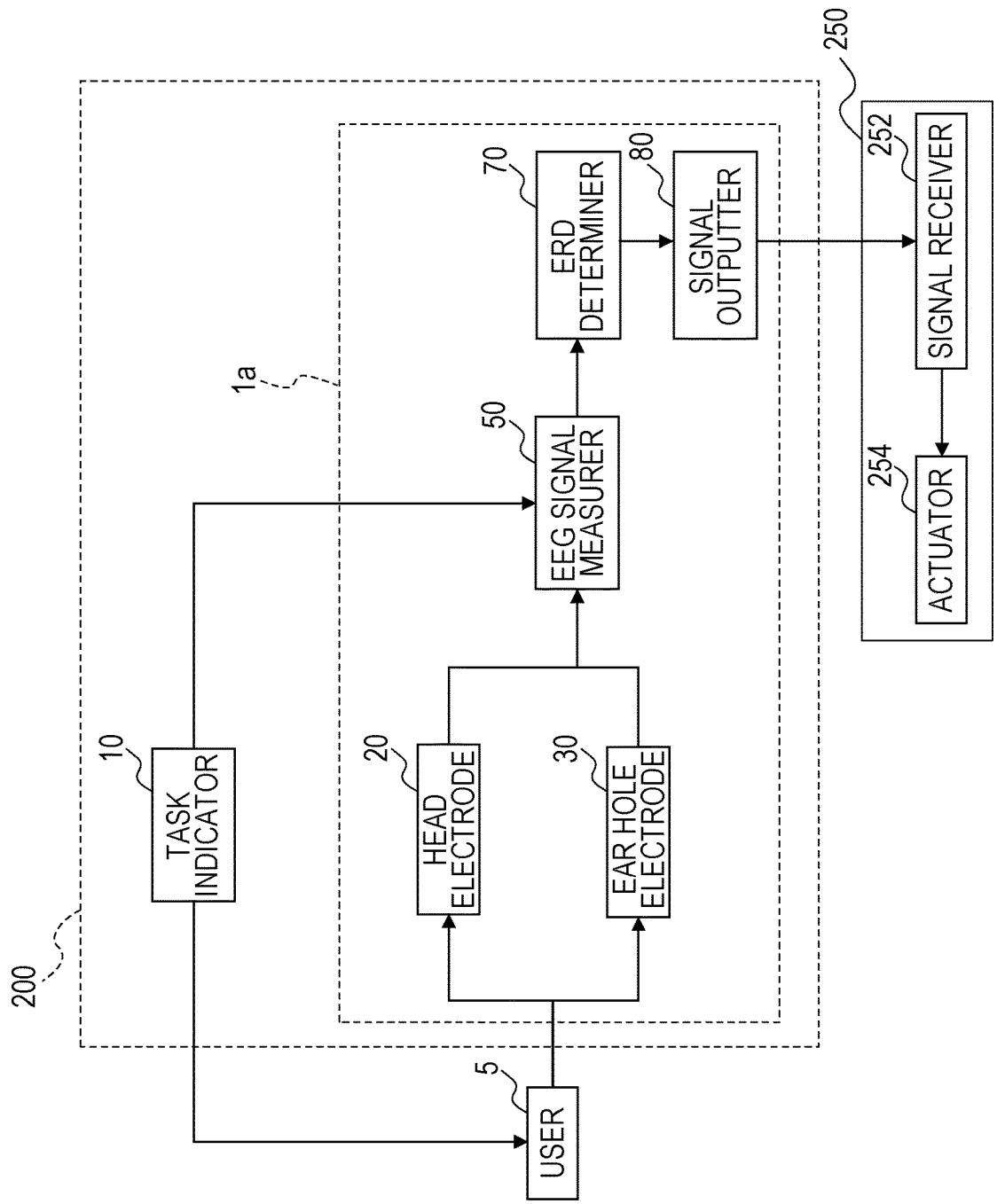
FIG. 13 is a diagram illustrating an example configuration of a rehabilitation system.
Figure 14:
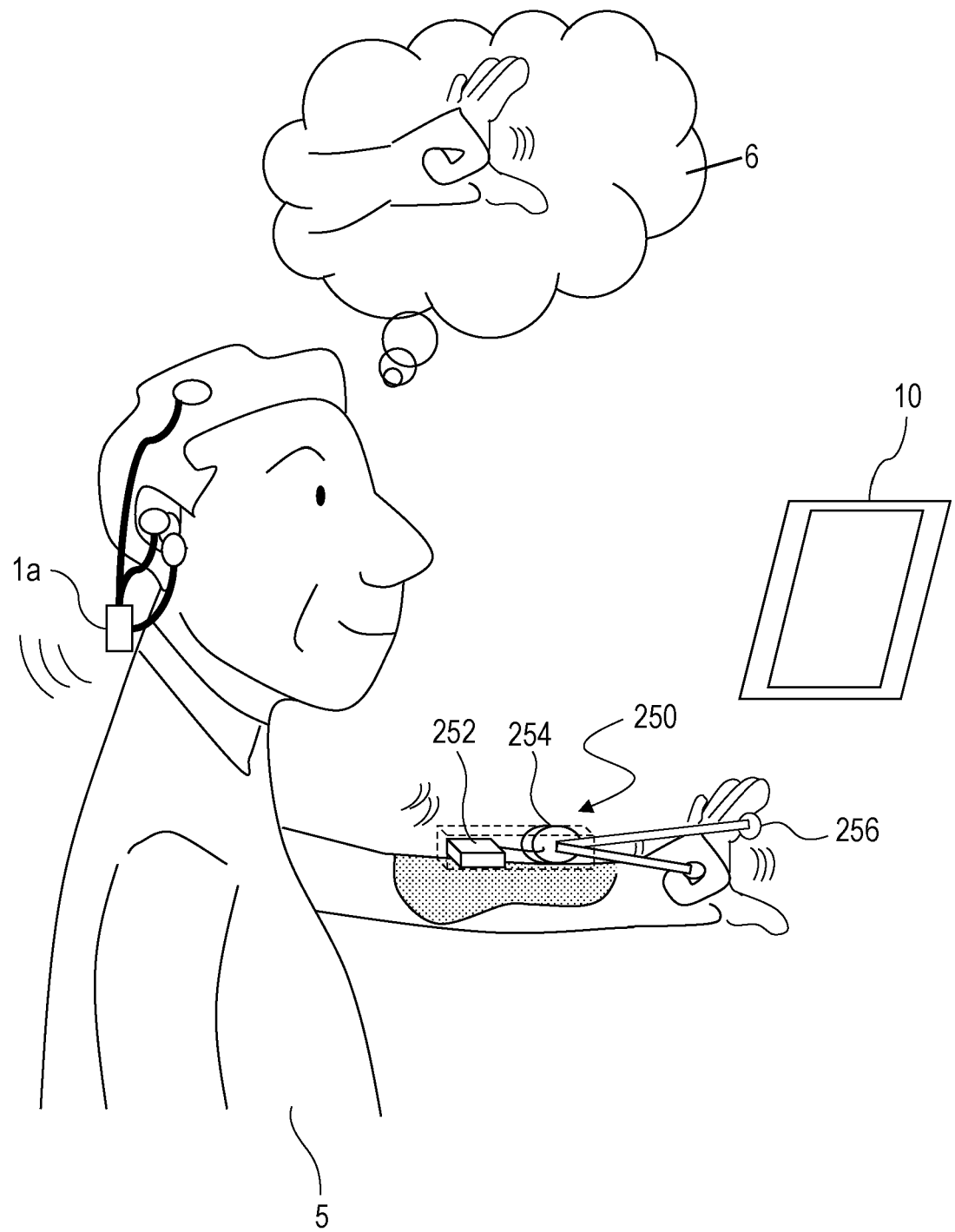
FIG. 14 is a diagram illustrating an environment in which the rehabilitation system is used.

FIG. 13 illustrates an example configuration of a rehabilitation system 300. The rehabilitation system 300 includes a control signal output system 200 and a rehabilitation assistance apparatus 250. FIG. 14 illustrates an environment in which the rehabilitation system 300 is used. It is assumed that the user 5 who uses the rehabilitation system 300 has paralyzed fingers and is unable to move the fingers with his/her intention. FIG. 13 includes a thought bubble 6 that is a representation of a motor intention of the user 5.

In the rehabilitation system 300, the user 5 is wearing the rehabilitation assistance apparatus 250. The rehabilitation assistance apparatus 250 is provided with an actuator 254. The actuator 254 is capable of causing the hand of the user 5 to open or close by, for example, driving a bar 256 held by the user 5 up and down. The bar 256 is an example of an attachment attached to the user 5. The attachment can vary in accordance with the aim of rehabilitation performed by a user.

An ERD measurement apparatus 1a of the rehabilitation system 300 outputs a control signal for driving the actuator 254 if it is determined that ERD exists in brain waves of the user 5. As described above, if it is determined that ERD exists, it means that a motor intention related to the right side or left side of the body of the user 5 is included in the brain waves of the user 5. The control signal is received by a signal receiver 252 of the rehabilitation assistance apparatus 250. The received control signal is transmitted to the actuator 254 and is used to drive the actuator 254.

The actuator 254 is driven in synchronization with detection of an intention of the user 5, and thereby the user's hand is opened or closed. Accordingly, the motor nerve of the user 5 is stimulated. Since the user's fingers are stimulated at the timing when an intention is generated, a rehabilitation effect of improving the function of paralyzed fingers of the user 5 can be expected.

Referring back to FIG. 13, the control signal output system 200 outputs a control signal for controlling the operation of the above-described rehabilitation assistance apparatus 250.

The control signal output system 200 is different from the above-described ERD measurement system 100 in that the control signal output system 200 further includes a signal outputter 80. In FIG. 13, the configuration in which the signal outputter 80 is added to the above-described ERD measurement apparatus 1 is illustrated as the ERD measurement apparatus 1a. Hereinafter, only the configuration related to the difference will be described. The configurations and functions of the other components illustrated in FIG. 13 are the same as those illustrated in FIG. 10 and thus the description thereof is omitted.

The signal outputter 80 transmits a control signal corresponding to a determination result generated by the ERD determiner 70 to the rehabilitation assistance apparatus 250. In FIG. 14, the signal outputter 80 transmits the control single in a wireless manner, but the signal outputter 80 may transmit the control signal in a wired manner.

The rehabilitation assistance apparatus 250 includes the signal receiver 252 and the actuator 254. Regarding the bar 256 as an attachment (FIG. 14), only the overview is described.

The signal receiver 252 is a reception circuit that receives a control signal output from the signal outputter 80. In this embodiment, wireless communication performed by the signal outputter 80 and the signal receiver 252 conforms to, for example, the standard of Bluetooth (registered trademark). The signal receiver 252 extracts a control signal from the received signal and transmits the control signal to the actuator 254. The actuator 254 drives the bar 256 in accordance with the control signal.

Figure 15:
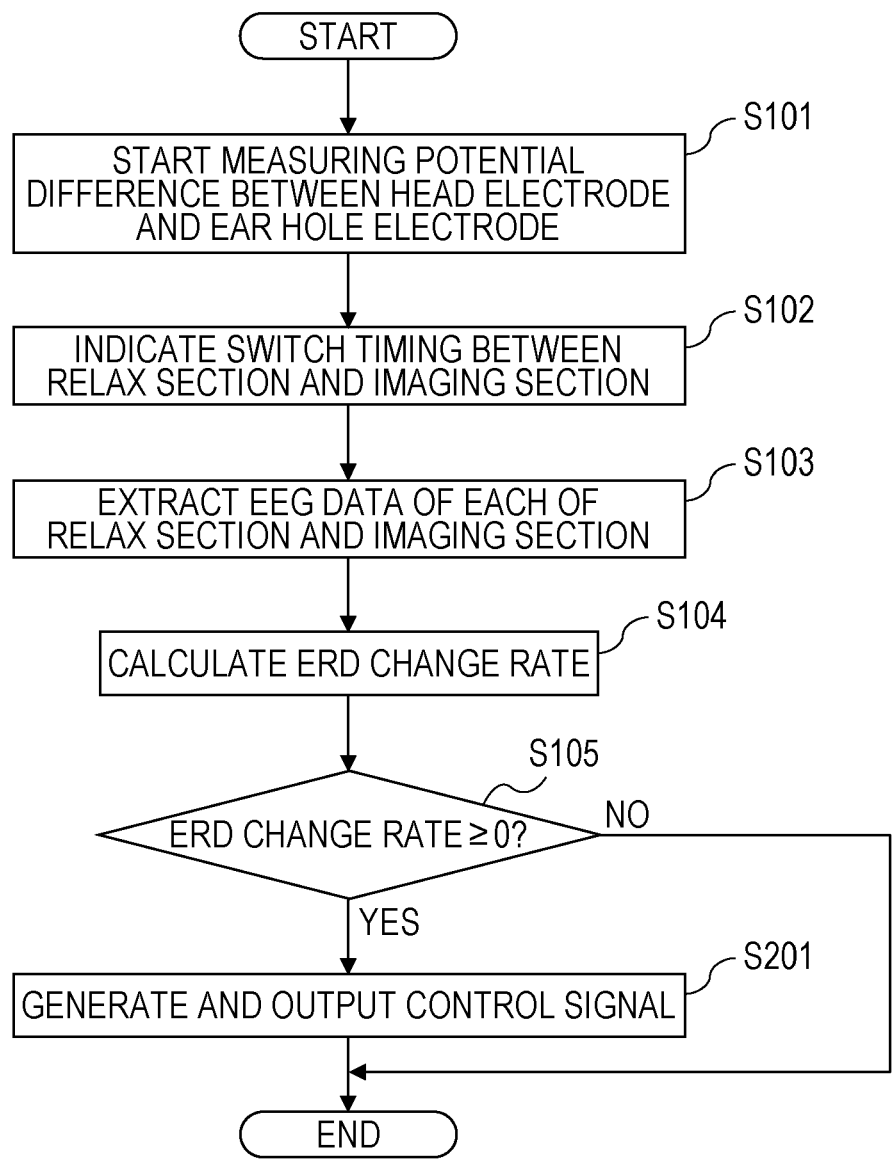
FIG. 15 is a flowchart illustrating a procedure of processing performed by a control signal output system of the rehabilitation system.

FIG. 15 is a flowchart illustrating a procedure of processing performed by the control signal output system 200 of the rehabilitation system 300. The flowchart in FIG. 15 is different from that in FIG. 12 in that step S201 is provided instead of steps S106 and S107 in FIG. 12.

Step S201 is performed if the ERD change rate is a positive value or zero, that is, if ERD exists. The signal outputter 80 generates a control signal for driving the actuator 254 and outputs the control signal. How the actuator 254 is specifically driven by this control signal varies in accordance with the type of attachment and a rehabilitation program. In this embodiment, the control signal is used for driving the actuator 254 that drives the bar 256 up and down.

If the ERD change rate is not a positive value or zero in step S201, a control signal is not generated and the processing ends.

Figure 16:
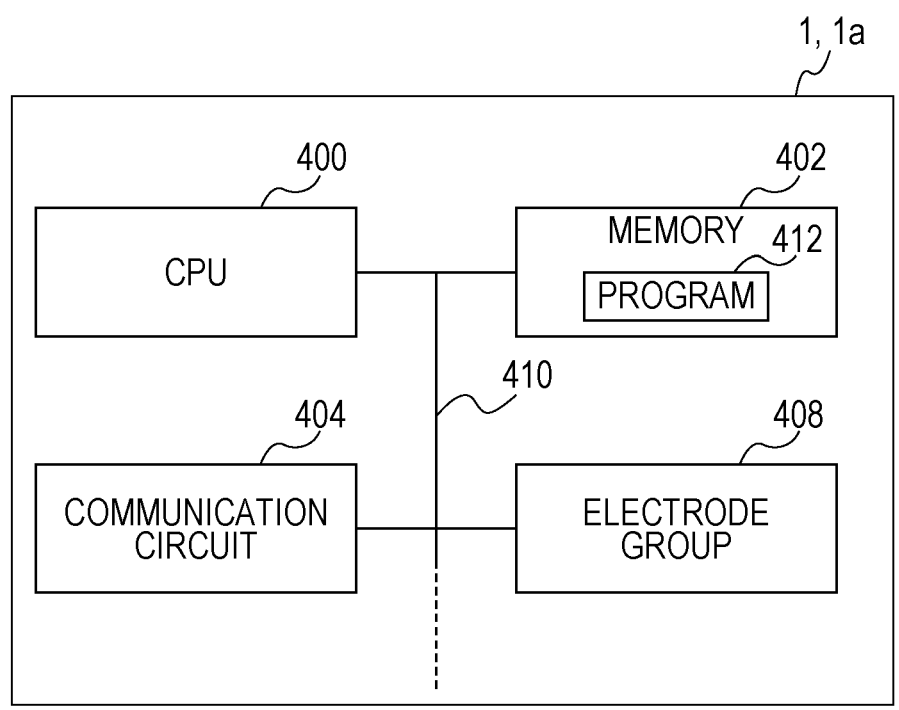
FIG. 16 is a diagram illustrating an example of the hardware configuration of an ERD measurement apparatus.

FIG. 16 illustrates an example of the hardware configuration of the above-described ERD measurement apparatus 1 or 1a.

The ERD measurement apparatuses 1 and 1a each include a central processing unit (CPU) 400, a memory 402, a communication circuit 404, and an electrode group 408. The CPU 400, the memory 402, the communication circuit 404, and the electrode group 408 are connected to one another via a bus 406 and are capable of receiving data from and transmitting data to one another.

The CPU 400 executes a computer program 412 stored in the memory 402 and thereby functions as the EEG signal measurer 50 and the ERD determiner 70. In the computer program 412, a procedure for causing the individual components to perform the processing illustrated in the above-described flowchart (FIG. 12 or FIG. 15) is described. The ERD measurement apparatuses 1 and 1a perform the above-described operation in accordance with the computer program 412.

The communication circuit 404 is a circuit that communicates with an external apparatus in a wireless or wired manner by using a predetermined communication protocol. For example, the communication circuit 404 receives information and a label specifying a relax section and information and a label specifying a movement imaging section from a tablet terminal serving as the task indicator 10. The communication circuit 404 in the ERD measurement apparatus 1a also functions as the signal outputter 80 that outputs a control signal.

The EEG signal measurer 50 and the ERD determiner 70 of the ERD measurement apparatuses 1 and 1a may be implemented as hardware such as a digital signal processor (DSP) in which a computer program is loaded in one semiconductor circuit.

The above-described computer program 412 may be recorded on a recording medium such as a CD-ROM and circulated in the market as a product, or may be transmitted through an electric communication network such as the Internet. The apparatus including the hardware illustrated in FIG. 16 (for example, a personal computer (PC)) can function as the ERD measurement apparatus 1 or the ERD measurement apparatus 1a by reading the computer program 412.

With an ERD measurement system according to an exemplary embodiment of the present disclosure, ERD can be detected with high accuracy by using a differential waveform of brain waves recorded by using a head electrode at one point around the motor area of the head portion on the side opposite to a movement imaging hand of a user and an ear hole electrode at one point in an ear hole. Accordingly, the effect of BMI rehabilitation using an EEG is significantly increased.

What is claimed is:

1. A determination system comprising:
    a head electrode that is configured to be located on a left head portion of a user;
    an ear hole electrode that is configured to be located in an ear hole of the user;
    a memory configured to store a program; and
    a processor configured to execute the program and control the determination system to:
    obtain a voltage signal between the head electrode and the ear hole electrode; and
    determine whether or not a change in the voltage signal indicates that the user intends to move a portion on a right side of the body of the user.

2. The determination system according to claim 1, wherein, in a case where the change in the voltage signal is a first threshold or larger, the processor is further configured to execute the program and control the determination system to determine that the change in the voltage signal indicates that the user intends to move the portion on the right side of the body of the user.

3. The determination system according to claim 1, wherein the ear hole electrode is configured to be located in the ear hole of the user which includes an auricular concha or an external auditory canal.

4. The determination system according to claim 1, further comprising:
    an indicator that indicates, to the user, a first time section in which the user has a motor intention and a second time section in which the user does not have a motor intention,
    wherein, in a case where a frequency band power of the voltage signal in a certain frequency band in the first time section is smaller than a frequency band power of the voltage signal in the certain frequency band in the second time section, the processor is further configured to execute the program and control the determination system to determine that the voltage signal indicates that the user intends to move the portion on the right side of the body of the user.

5. The determination system according to claim 4, wherein the voltage signal includes a first voltage signal observed in the first time section and a second voltage signal observed in the second time section.

6. The determination system according to claim 4, wherein the frequency band is included in a band from 8 to 25 Hz.

7. The determination system according to claim 4, wherein the frequency band includes an α waveband and a β waveband.

8. The determination system according to claim 1, wherein the ear hole electrode is located in a right ear hole.

9. The determination system according to claim 1, wherein a reference electrode is configured to be located on a left mastoid of the user.

10. A control signal output system, comprising:
    a head electrode that is configured to be located on a left head portion of a user;
    an ear hole electrode that is configured to be located in an ear hole of the user;
    an electroencephalogram signal measurer that obtains a voltage signal between the head electrode and the ear hole electrode; and
    a signal outputter that outputs a control signal for operating an actuator that operates an attachment that is attached to the user and assists movement of the user in accordance with a change in the voltage signal.

11. The control signal output system according to claim 10, wherein, in a case where the change in the voltage signal is a first threshold or larger, the signal outputter outputs the control signal.

12. The control signal output system according to claim 10, wherein the ear hole electrode is configured to be located in the ear hole of the user which includes an auricular concha or an external auditory canal.

13. The control signal output system according to claim 10, further comprising:
    an indicator that indicates, to the user, a first time section in which the user has a motor intention and a second time section in which the user does not have the motor intention,
    wherein, in a case where a frequency band power of the voltage signal in a certain frequency band in the first time section is smaller than a frequency band power of the voltage signal in the certain frequency band in the second time section, the signal outputter outputs the control signal.

14. A rehabilitation system comprising:
    an attachment that is attached to a user and assists movement of the user;
    an actuator that operates the attachment;
    a head electrode that is configured to be located on a left head portion of the user;
    an ear hole electrode that is configured to be located in an ear hole of the user;
    an electroencephalogram signal measurer that obtains a voltage signal between the head electrode and the ear hole electrode; and
    a signal outputter that outputs a control signal for operating the actuator in accordance with a change in the voltage signal.

15. The rehabilitation system according to claim 14, wherein, in a case where the change in the voltage signal is a first threshold or larger, the signal outputter outputs the control signal.

16. The rehabilitation system according to claim 14, wherein the ear hole electrode is configured to be located in the ear hole of the user which includes an auricular concha or an external auditory canal.

17. The rehabilitation system according to claim 14, further comprising:

an indicator that indicates, to the user, a first time section in which the user has a motor intention and a second time section in which the user does not have the motor intention, wherein, in a case where a frequency band power of the voltage signal in a certain frequency band in the first time section is smaller, by a second threshold or larger, than a frequency band power of the voltage signal in the certain frequency band in the second time section, the signal outputter outputs the control signal.

18. A determination method comprising:

obtaining a voltage signal between a head electrode and an ear hole electrode by using the head electrode and the ear hole electrode, the head electrode being located on a left head portion of a user, the ear hole electrode being located in an ear hole of the user; and determining whether or not a change in the voltage signal indicates that the user intends to move a portion on a right side of the body of the user.

19. A control signal output method, comprising:

obtaining a voltage signal between a head electrode and an ear hole electrode by using the head electrode and the ear hole electrode, the head electrode being located on a left head portion of the user, the ear hole electrode being located in an ear hole of the user; and outputting a control signal for operating an actuator that operates an attachment that is attached to the user and assists movement of the user in accordance with a change in the voltage signal.

20. A recording medium storing a computer program that causes a computer to perform processing, the recording medium being non-volatile and computer-readable, the processing comprising:

obtaining a voltage signal between a head electrode and an ear hole electrode by using the head electrode and the ear hole electrode, the head electrode being located on a left head portion of a user, the ear hole electrode being located in an ear hole of the user; and determining whether or not a change in the voltage signal indicates that the user intends to move a portion on a right side of the body of the user.

21. A recording medium storing a computer program that causes a computer to perform processing, the recording medium being non-volatile and computer-readable, the processing comprising:

obtaining a voltage signal between a head electrode and an ear hole electrode by using the head electrode and the ear hole electrode, the head electrode being located on a left head portion of the user, the ear hole electrode being located in an ear hole of the user; and outputting a control signal for operating an actuator that operates an attachment that is attached to the user and assists movement of the user in accordance with a change in the voltage signal.

* * * * *